United States Patent
Roy

(10) Patent No.: US 7,074,235 B1
(45) Date of Patent: Jul. 11, 2006

(54) LOW-PROFILE, NON-STENTED PROSTHESIS FOR TRANSLUMINAL IMPLANTATION

(76) Inventor: Sumit Roy, Vœkerøveien 106, Oslo (NO) N-0257

( * ) Notice: Subject to any disclaimer, the term of this patent is extended or adjusted under 35 U.S.C. 154(b) by 214 days.

(21) Appl. No.: 10/110,900

(22) PCT Filed: Oct. 16, 2000

(86) PCT No.: PCT/NO00/00337

§ 371 (c)(1),
(2), (4) Date: Apr. 23, 2002

(87) PCT Pub. No.: WO01/28453

PCT Pub. Date: Apr. 26, 2001

Related U.S. Application Data

(60) Provisional application No. 60/159,920, filed on Oct. 16, 1999.

(51) Int. Cl.
*A61F 2/06* (2006.01)

(52) U.S. Cl. .................. 623/1.11; 623/1.12; 623/1.23; 606/108

(58) Field of Classification Search .......... 623/1.1–1.2, 623/1.32–1.35, 1.11, 1.12, 1.13, 1.14, 1.15, 623/1.23; 606/108
See application file for complete search history.

(56) References Cited

U.S. PATENT DOCUMENTS

| | | | | |
|---|---|---|---|---|
| 5,089,006 | A | * | 2/1992 | Stiles .......................... 623/1.1 |
| 5,151,105 | A | * | 9/1992 | Kwan-Gett ................. 623/1.32 |
| 5,540,712 | A | * | 7/1996 | Kleshinski et al. ......... 623/1.19 |
| 5,713,917 | A | * | 2/1998 | Leonhardt et al. .......... 606/194 |
| 5,713,948 | A | * | 2/1998 | Uflacker ..................... 623/1.23 |
| 5,776,186 | A | | 7/1998 | Uflacker |
| 5,908,410 | A | * | 6/1999 | Weber et al. ................ 604/523 |
| 5,951,566 | A | * | 9/1999 | Lev ............................. 606/108 |
| 6,015,422 | A | | 1/2000 | Kerr |

(Continued)

OTHER PUBLICATIONS

Resch T, et al. Distal migration of stent-grafts after endovascular repair of abdominal aortic aneurysms J Vasc Interv Radiol 1999 10: 257-264.
Kerr A. Slim graft: a low-profile method for deploying endovascular grafts J Vasc Interv Radiol 1999 10: 281-284.
Sakaguchi S, et. al. Twin-tube endografts for aortic aneurysms: an experimental feasibility study. J Vasc Interv Radiol 1999 10: 1092-1098.
Quinn SF, et. al. Percutaneous deployment of a low-profile bifurcated stent-graft . Am J Roentgenol 2002: 178:654-656.

*Primary Examiner*—Bruce Snow
*Assistant Examiner*—Cheryl Miller

(57) ABSTRACT

An implantable prosthesis for placement in hollow tubular organs is described alongwith an instrument for deploying the said prosthesis. On radial compaction, the prosthesis has a low profile, allowing introduction into the body with a deployment instrument of low calibre. The prosthesis has a longitudinal strut to provide longitudinal support. One or more, outwardly biased, flexible curvilinear members with good shape-memory, symmetrically attached to the leading end of the prosthesis help unroll the prosthesis during deployment. Magnetized wires or powder may be attached to the prosthesis to facilitate this process and provide in addition radial elasticity to the prosthesis. The prosthesis may have tubular extensions to allow the treating lesions that involve the parent tubular organ and its branches. Alternatively, the prosthesis may be provided with apertures which can be widened in vivo. For implantation in branches, the prosthesis may be provided with a flange at its trailing end.

17 Claims, 19 Drawing Sheets

U.S. PATENT DOCUMENTS

| | | | |
|---|---|---|---|
| 6,149,681 A * | 11/2000 | Houser et al. | 623/1.12 |
| 6,165,214 A * | 12/2000 | Lazarus | 623/1.35 |
| 6,214,036 B1 * | 4/2001 | Letendre et al. | 623/1.11 |
| 6,224,626 B1 * | 5/2001 | Steinke | 623/1.16 |
| 6,322,588 B1 * | 11/2001 | Ogle et al. | 623/1.46 |
| 6,346,118 B1 * | 2/2002 | Baker et al. | 623/1.12 |
| 6,395,018 B1 * | 5/2002 | Castaneda | 623/1.13 |
| 6,503,271 B1 * | 1/2003 | Duerig et al. | 623/1.15 |

* cited by examiner

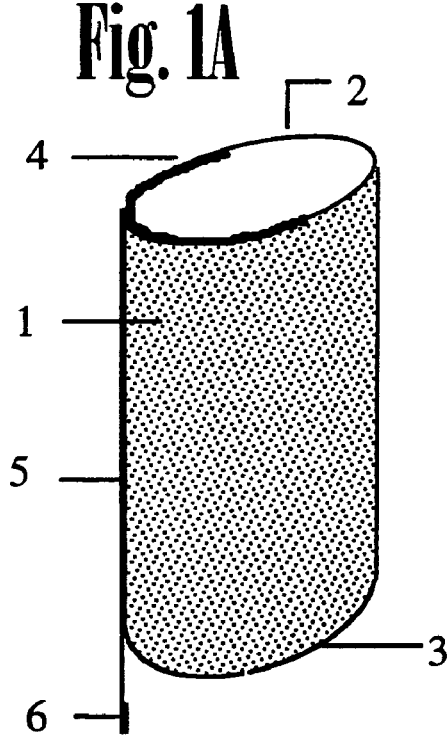
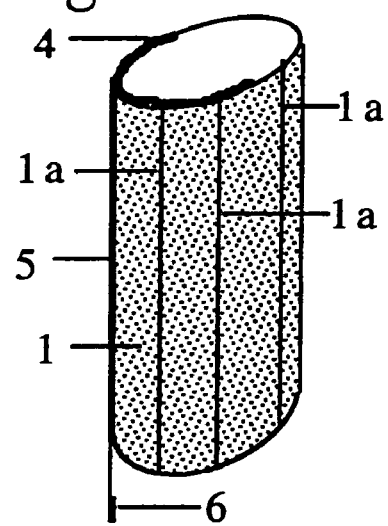
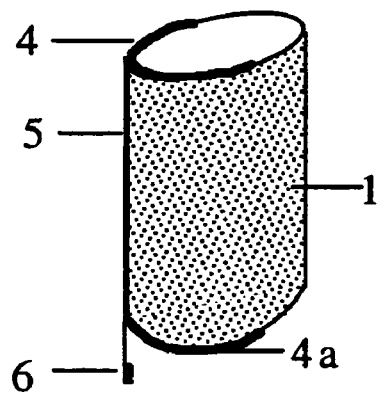
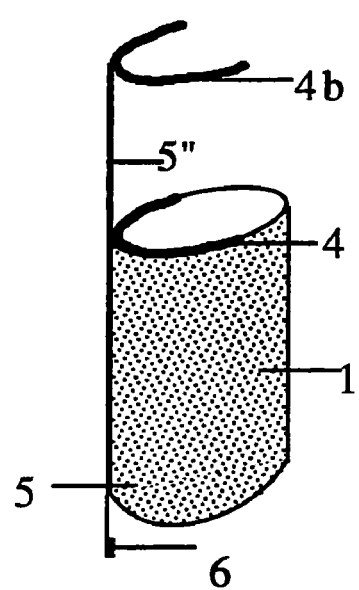

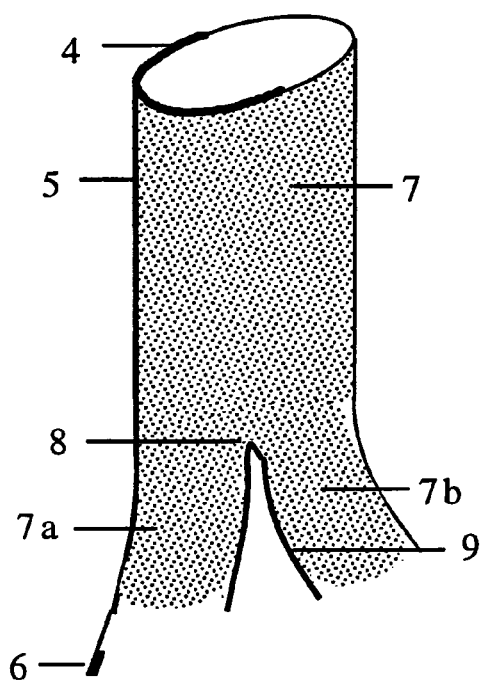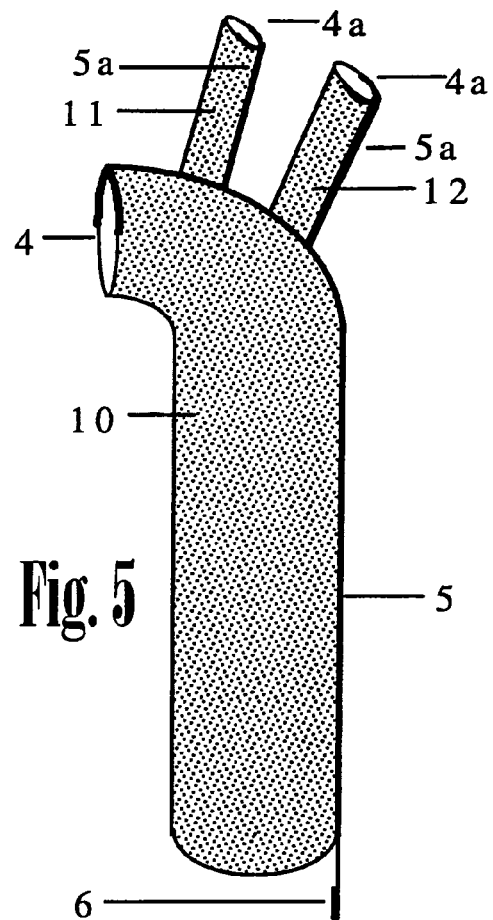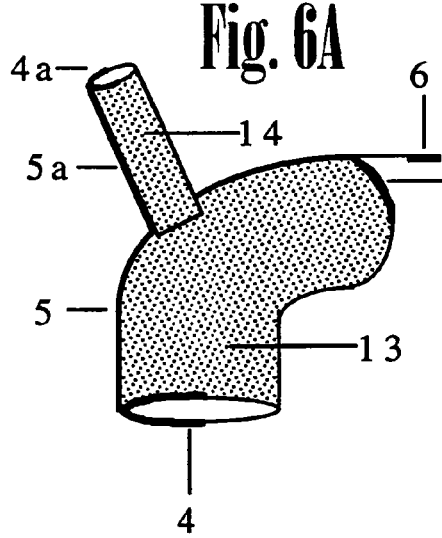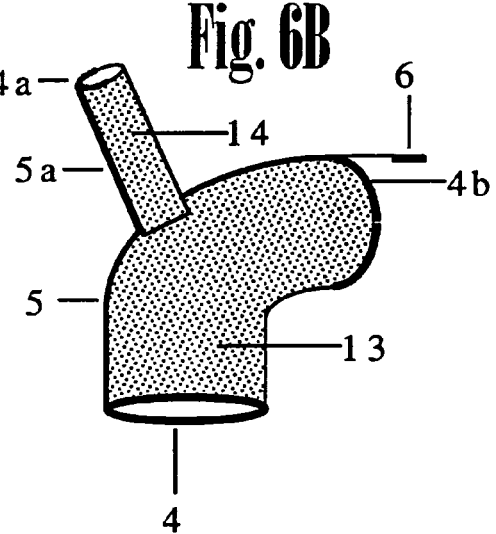

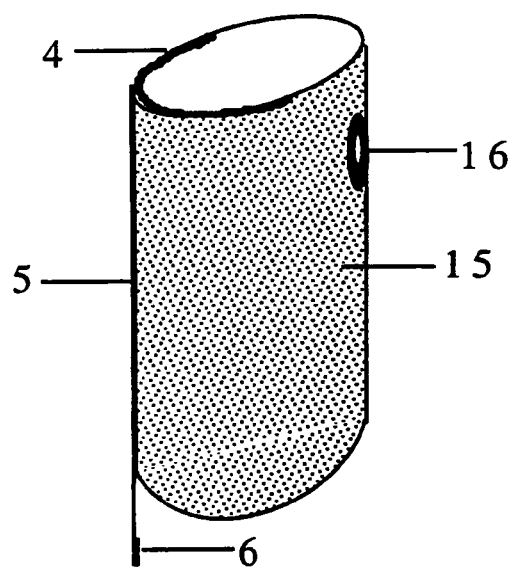
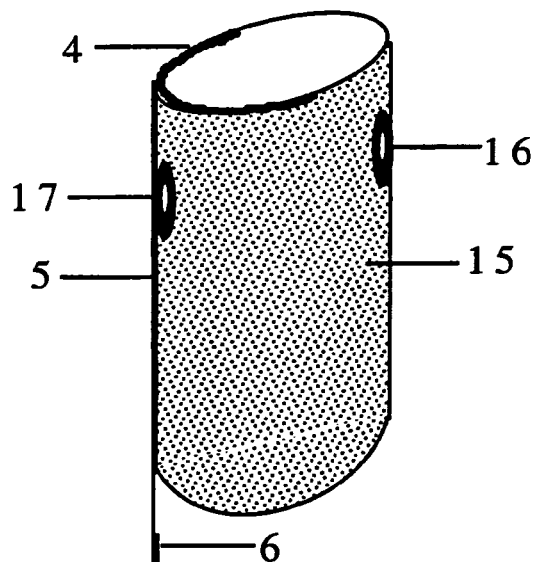
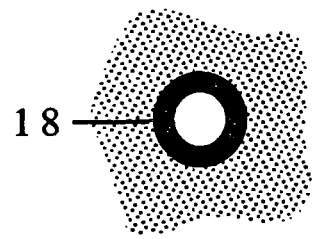
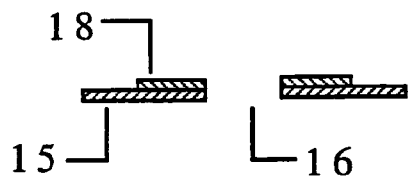
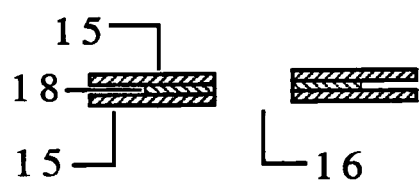

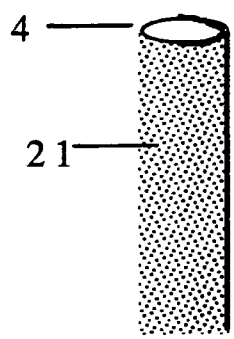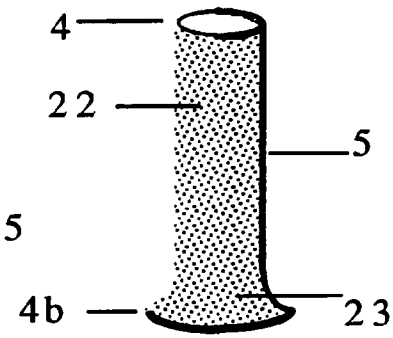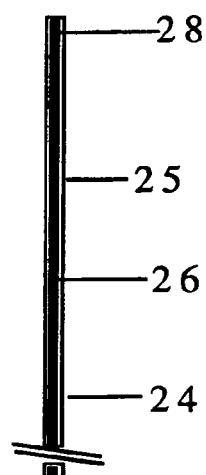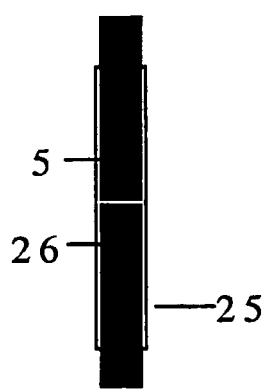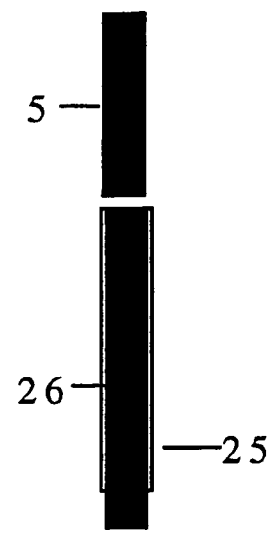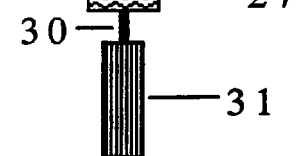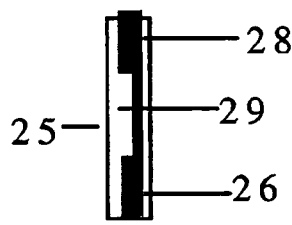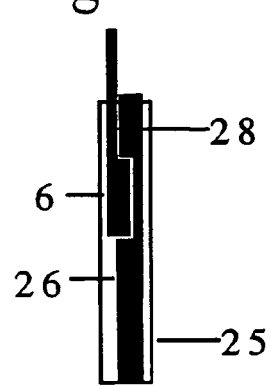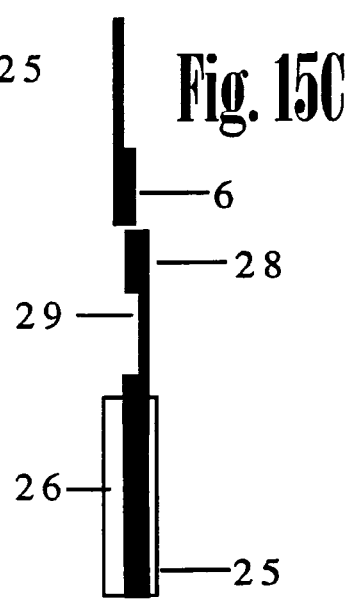

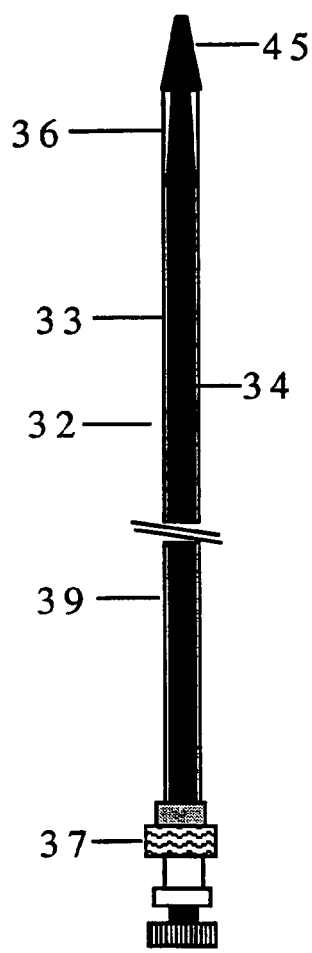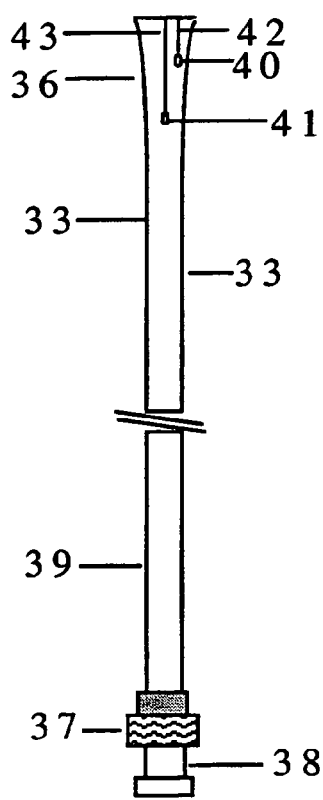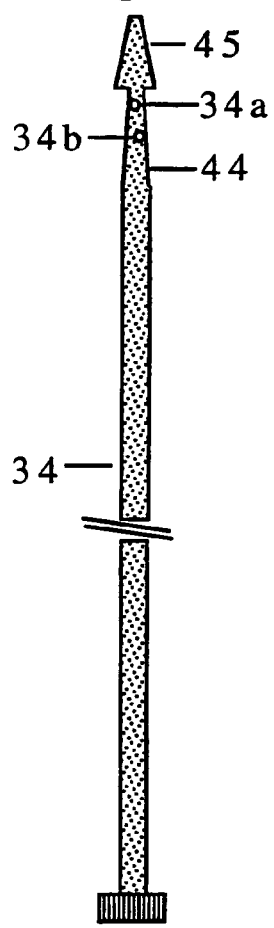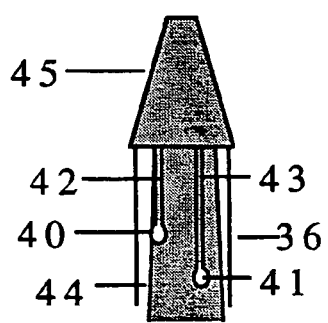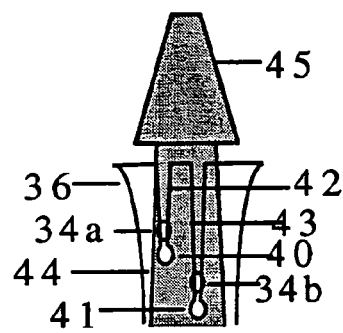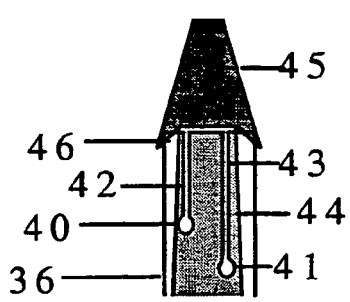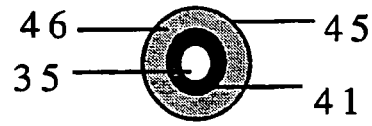

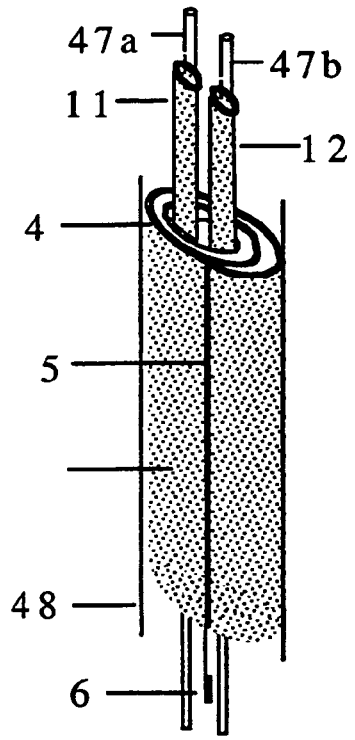
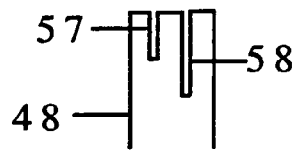
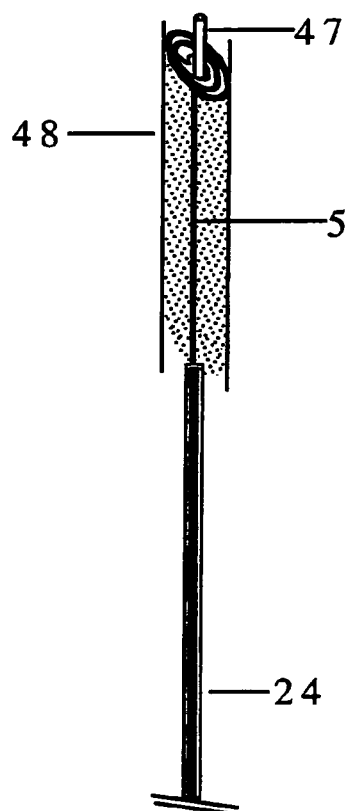
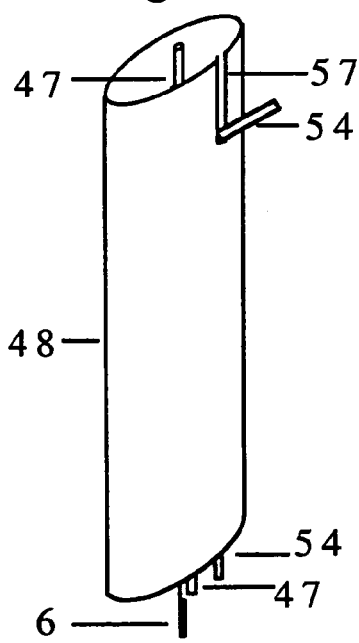
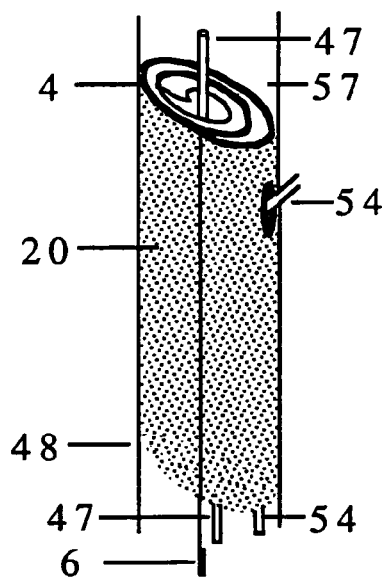
Fig. 26
Fig. 27
Fig. 28
Fig. 29
Fig. 30

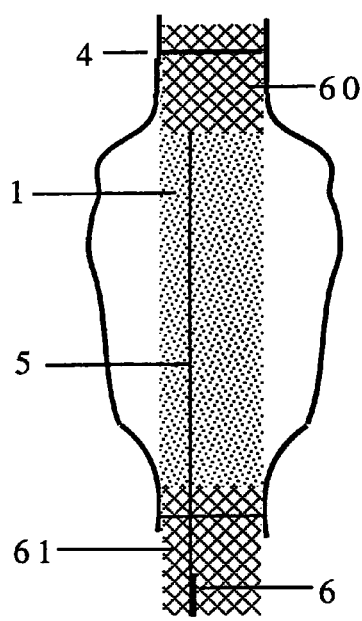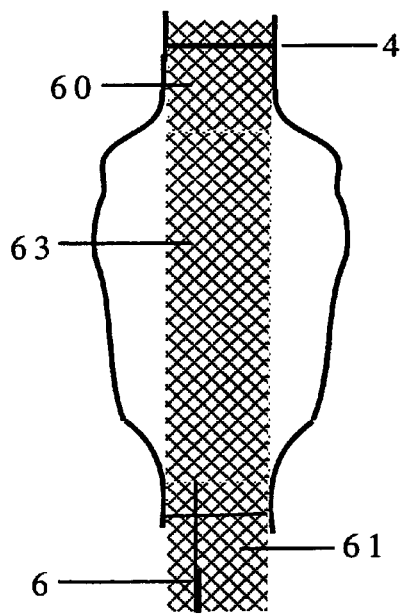

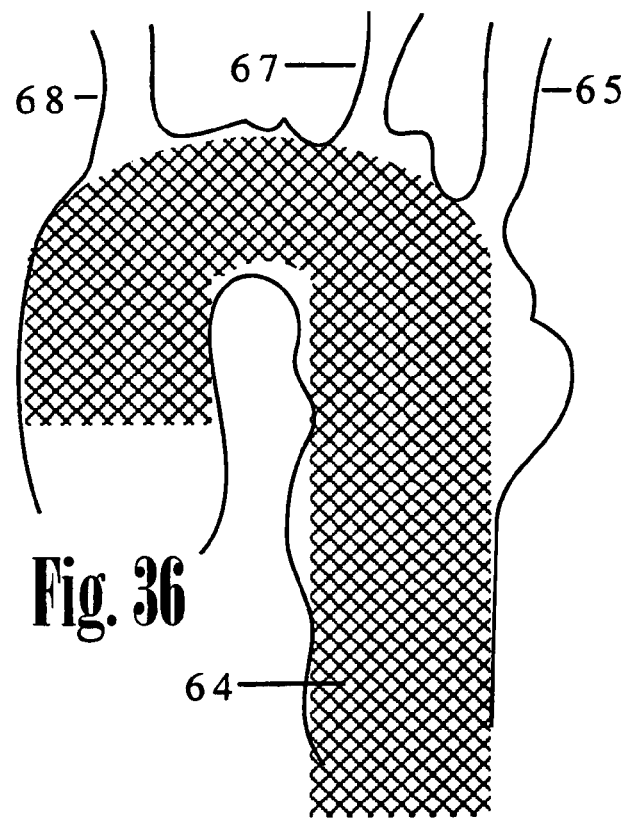
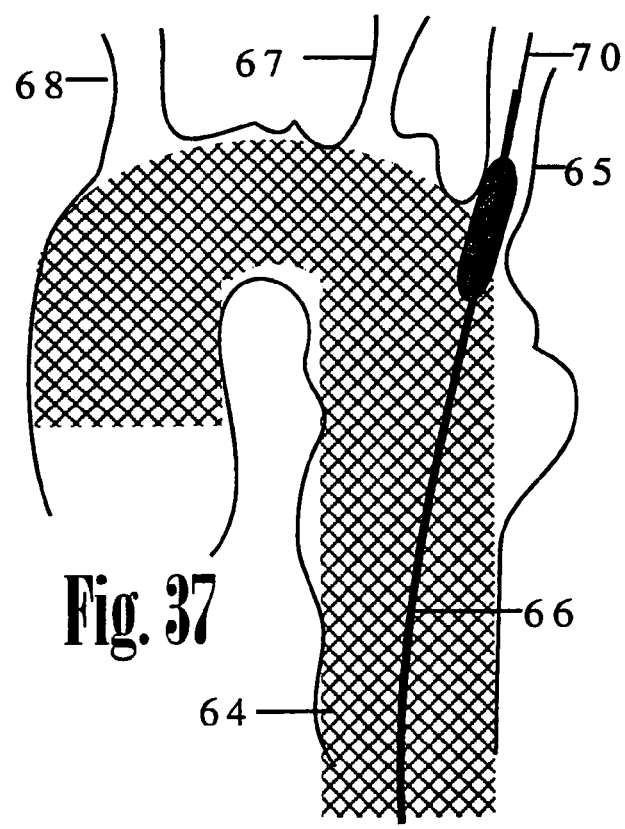

US 7,074,235 B1

LOW-PROFILE, NON-STENTED PROSTHESIS FOR TRANSLUMINAL IMPLANTATION

RELATED APPLICATION

This patent application claims priority from U.S. Provisional Patent Application Ser. No. 60/159,920, filed on Oct. 16, 1999, the entire disclosure of the application being expressly incorporated herein by reference.

TECHNICAL FIELD

This invention under consideration concerns a prosthetic device and related instrument for non-surgically treating diseases of tubular organs of the human body, and methods for using the using the said prosthesis for the said purpose.

BACKGROUND ART

Over the past two decades, treatment of diseases by the transluminal placement of a prosthesis has garnered increasing attention. In the field of vascular disease, this therapeutic modality now represents the intervention of choice for most occlusive lesions. The satisfactory results obtained with this treatment strategy has encouraged its application for the management of lesions such as aneurysms which are characterized by partial or complete loss of structural integrity rather than hindrance to blood flow. Beginning with U.S. Pat. No. 4,140,126, multiple prostheses have been described for the purpose, some of which the stage of clinical trial. Experience with these prostheses has demonstrated that while they do have therapeutic value, all suffer from a common drawback. They are too bulky to be implanted without creating a surgical vascular access, thereby negating one of the major advantages of the transluminal approach. This characteristic also make them difficult to implant in patients with tortuous blood vessels. Another limitation associated with the use of these prostheses is the inability to treat lesions involving the craniocerebral or visceral branches of the aorta. That the prostheses in use have the same disadvantage is not a coincidence because all are based on the same underlying design: a flexible non-porous tube braced by an expandable metallic skeleton. Reducing the metallic skeleton to a single, sturdy metallic collar has been proposed as one way to reduce the bulk of a prostheses during introduction (PCT International Application WO 97/48350). While this modification certainly makes for a more streamlined device, it does not eliminate the need for surgically creating a vascular access because the introducer catheter required has an outer diameter of is approximately 5 mm (15 Fr). Furthermore, clinical experience indicates that the absence of support along the longitudinal axis of the device is likely to increase the risk of complications associated with its use such as migration (Resch T. et. al. J Vasc Interv Radiol 1999; 10:257–64).

Deployment of the tubular component of the prosthesis and its metallic skeleton in sequence suggests itself as a possible solution to the problem. A retrievable prosthesis comprising a flexible polymer tube provided with two encircling resilient loops for temporary fixation attached independently to two metals leads during implantation is the subject of U.S. Pat. No. 5,776,186. The inherent resistance of a resilient loop to deformation limits the degree to which the prosthesis can be compacted during delivery into the arterial system. Besides, the presence of two manipulation leads running along the length of the prosthesis and the relatively complex and bulky mechanism for attaching them to the prosthesis, and the presence of the mechanism radially adjacent to the prosthesis further increases the profile of the device making it necessary for the introducer catheter to be at least 12 Fr in size (OD≈3.8 mm). This requirement mandates the surgical opening of a blood vessel for placement of the prosthesis. The prosthesis also lacks any intrinsic longitudinal support once the manipulation leads are withdrawn following implantation, detracting from its potential safety profile (Resch T. et. al. J Vasc Interv Radiol 1999; 10:257–64). Furthermore, in common with currently available prostheses, it cannot be used for treating aortic disease involving the craniocerebral, visceral, or renal branches. Perhaps for these reasons no reports about the use even in animal models has been published thus far in medical literature. Kerr described a conceptually similar prosthesis comprising a polymer tube supported by two bent guidewires each of which is bent to define a loop (U.S. Pat. No. 6,015,422). After the tube is deployed in the blood vessel and a stent coaxially implanted to anchor it, an expandable device such as an angioplasty catheter is used to break the loops allowing the guidewires to be withdrawn. As the prosthesis is not physically attached to the guidewires, the possibility exists of inadvertent separation of the prosthesis from the latter from the latter during delivery. Further in common with the invention covered U.S. Pat. No. 5,776, 186, and cited above, the resilient loops limit the degree to which the prosthesis can be compacted during delivery into the target organ. In an alternative embodiment two guidewires are provided which are bent to form two outwardly-biased tines that are attached to the prosthesis with threads. Expanding the prosthesis with a device such as an angioplasty catheter tears the threads allowing the withdrawal of the guidewires. On the basis of published data, neither does this embodiment promise a materially more streamlined profile during delivery, as the introducer catheter 12.9 Fr (O.D.≈4.1 mm) in calibre is required for deployment (Kerr A. J Vasc Interv Radiol 1999; 10:281–4). The mechanism used for detaching the prosthesis carries the risk of damaging the prosthesis. Furthermore the prosthesis is not suitable for treating aortic disease involving the craniocerebral, visceral, or renal branches.

Thus there exists a need for a prosthesis for transluminal implantation that has a low enough profile to be introduced into the body by the non-surgical, percutaneous, approach and yet has sufficient longitudinal rigidity to minimise the risk of complications. In addition the prosthesis should be suitable for treating vascular lesions involving the aorta and its craniocerebral, visceral, or renal branches. These requirements are fulfilled by the invention under consideration.

BRIEF DESCRIPTION OF THE DRAWINGS

To facilitate understanding, throughout the description, the adjective "leading" identifies the end or edge of an object, such as a prosthesis or device, that precedes the rest of said object, when said object is being introduced into another object such as the human body.

FIG. 1A is a perspective view of the preferred embodiment of the implantable prosthesis FIG. 1B is a perspective view of an alternative embodiment of the implantable prosthesis incorporating magnetised struts FIG. 2 is a perspective view of an alternative embodiment of the implantable prosthesis, characterized by curvilinear members attached to the leading edge and the trailing edge of the prosthesis FIG. 3 is a perspective view of an alternative embodiment of the implantable prosthesis with additional curvilinear members attached to the proximal free edge of the prosthesis via a linear member FIG. 4 is a perspective view of a branched embodiment of the implantable prosthesis for deployment in a organ at its bifurcation FIG. 5 is a perspective view of an branched embodiment of the implantable prosthesis for deployment in a organ and its branches FIG. 6A is a perspective view of an alternative branched embodiment of the implantable prosthesis for deployment in an organ and its branch, characterized by curvilinear members attached to the leading edge and the trailing edge of the prosthesis FIG. 6B is a perspective view of an alternative branched embodiment of the implantable prosthesis for deployment in a organ and its branch, characterized by curvilinear members being attached to the edges of the prosthesis along the entire circumference of the prosthesis FIG. 7A is a perspective view of an alternative embodiment of the implantable prosthesis, characterized by one aperture FIG. 7B is a perspective view of an alternative embodiment of the implantable prosthesis, characterized by multiple apertures FIG. 8A is a end-on view of an aperture of an implantable prosthesis FIGS. 8B & 8C are transverse sectional views through alternative embodiments of an aperture of an implantable prosthesis FIG. 11 is a perspective view of an alternative embodiment of the implantable prosthesis characterized by a supporting strut limited to the length of the prosthesis FIG. 12 is a perspective view of an alternative embodiment of the implantable prosthesis, characterized by a flanged trailing end FIG. 13 is a longitudinal sectional view of the delivery tool FIGS. 14A and 14B are respectively longitudinal sectional views of the leading end of the delivery tool before and after detachment of the implantable prosthesis FIG. 15A is a longitudinal sectional view of the leading end of an alternative embodiment of the delivery tool FIGS. 15B and 15C are respectively longitudinal sectional views of the leading end of the alternative embodiment of the delivery tool before and after detachment of the implantable prosthesis FIG. 16 is a longitudinal sectional view of the introducer catheter with its inner stiffening catheter in situ and locked to the introducer catheter FIG. 17 is a surface view of the introducer catheter without the inner stiffening catheter in situ FIG. 18 is a surface view of the inner stiffening catheter FIG. 19 is a longitudinal sectional view partly in section of the leading end of the introducer catheter with the inner stiffening catheter in situ and locked to the introducer catheter FIG. 20 is a longitudinal sectional view of the leading end of the introducer catheter after partial withdrawal of the inner stiffening catheter FIG. 21 is a longitudinal sectional view partly in section of the leading end of the introducer catheter with the inner stiffening catheter in situ and locked to the introducer catheter illustrating the engagement of the leading free edge of the introducer catheter in the sulcus at the base of the conical tip FIG. 22 is a transverse section through the sulcus of the leading end of a stiffening catheter FIG. 26 is a perspective view partly in section of a loading cartridge containing an implantable prosthesis with multiple branches FIG. 27 is a surface view of the leading end of a loading cartridge for an implantable prosthesis with multiple apertures FIG. 28 is a perspective view of a loading cartridge containing an implantable prosthesis with one aperture FIG. 29 is a perspective view partly in section of a loading cartridge containing an implantable prosthesis with one aperture FIG. 30 is a perspective view partly in section of an implantable prosthesis within its loading cartridge attached to its delivery tool FIGS. 32 to 35 are longitudinal sectional views illustrating the implantation of a prosthesis in an abdominal aorta with an aneurysm according to the invention FIGS. 36 to 45 are longitudinal sectional views illustrating the implantation of prostheses in a thoracoabdominal aorta with an aneurysm involving the craniocerebral branches according to the invention

DISCLOSURE OF THE INVENTION

DETAILED DESCRIPTION

Figure 9A:
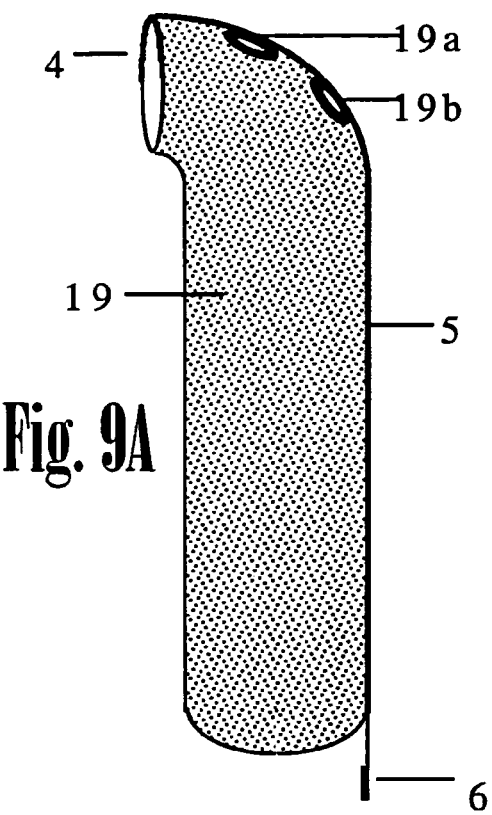
FIG. 9A is a perspective view of an alternative embodiment of the implantable prosthesis with multiple apertures

For the purpose of simplicity, the nomenclature selected for labelling some of the embodiments of the implantable prosthesis is of relevance to the arterial system. However as will be clear to anyone skilled in the art, the scope for the use of the prosthesis is not limited to the arterial system alone.

The invention is made from biocompatible materials. The materials used to make the components for permanent implantation are in addition characterised by long-term dimensional, structural, and configurational stability under cyclic loading.

The primary component of the invention is a uni- or multilamellar tube (tubular prosthesis) 1 with circular or elliptical cross-section, made from a flexible polymer (FIG. 1A). Multiple magnetised linear strips or wires (magnetic struts) 1a may be bonded to the prosthesis 1, parallel to the longitudinal axis of the prosthesis 1 (FIG. 1B). The strips 1a may be bonded to the inner or outer surface of the prosthesis 1, or sandwiched between two adjacent lamellae. The magnetic struts 1a are aligned and spatially arranged to ensure that radial centrifugal forces are exerted along the entire length of the prosthesis 1. The magnetised linear strips or wires may be substituted with symmetrical deposits of biocompatible magnetised particles. The particles may either be bonded to the tubular prosthesis 1 or impregnated in a resorbable biocompatible matrix that is bonded to the tubular prosthesis 1. The leading edge 2 and the trailing edge 3 of the prosthesis may or may not be parallel to each other, or perpendicular to the longitudinal axis of the tube. To the leading free edge 2 of the tube is symmetrically attached a pair of outwardly biased, flexible curvilinear members 4 made from a material with good shape memory; in one embodiment of the invention, curvilinear members are made from a thermodynamic material with a transitional temperature range below the normal human body temperature. To at least one of the curvilinear members 4 is attached a narrow strip or wire (supporting strut) 5 of a material stiffer than the prosthesis material. The support strut 5 is longer than the tubular prosthesis 1, and is bonded to the latter along its entire length, parallel to its long axis. The supporting strut is bonded to the inner or outer surface of the prosthesis 1, or sandwiched between two adjacent lamellae. The angle the curvilinear members 4 make with the supporting strut 5 is congruent to the angle the leading free edge 2 makes with the longitudinal axis of the tubular prosthesis 1. The angle between the curvilinear members 4 and the supporting strut 5 can be reversibly altered by the application of force perpendicular to the plane defined by the curvilinear members 4. On removal of the force, the curvilinear members 4 return to their original position. To the tip of the supporting strut may be attached a short, narrow, cylindrical peg (locking peg) 6 (FIGS. 1A,1B). The locking peg 6 has a larger cross-section than the supporting strut 5.

In an alternative embodiment of the prosthesis, one or more curvilinear members 4a, are also symmetrically attached to the trailing edge 3 of the tubular prosthesis 1 (FIG. 2). Curvilinear members 4b may also be attached to a prolongation 5" of the supporting strut beyond the leading edge of the prosthesis (FIG. 3). The modifications to the tubular prosthesis 1, described in this and the preceding paragraph may also be incorporated singly or in various combinations in the remaining embodiments of the prosthesis.

An alternative embodiment of the prosthesis (aortobifemoral prosthesis) 7 has a branched configuration as illustrated in FIG. 4. The crotch 8 and the two limbs 7a,7b of the prosthesis 7 are supported by a "V" shaped wire or strip (bifurcation supporting strut) 9 of a flexible material with good shape memory.

An alternative embodiment of the branched prosthesis (aortic arch-descending aorta prosthesis) 10 has the configuration as illustrated in FIG. 5, and is provided with two branches: left carotid limb 11, and left subclavian limb 12. Each branch 11,12 is provided with a longitudinal supporting strut 5a, and one or more outwardly biased, flexible curvilinear members with good shape memory 4a at its leading edge, at least one of which is attached to the supporting strut 5a.

An alternative embodiment of the branched prosthesis (ascending aorta-aortic arch prosthesis) 13 has the configuration illustrated in FIG. 6A and FIG. 6B, and is provided with one branch: the brachiocephalic limb 14. One or more outwardly biased, flexible curvilinear members with good shape memory 4,4b are symmetrically attached to the leading edge and the trailing edge of the prosthesis 13. At least one of the curvilinear members attached to each free edge is attached to or continuous with the supporting strut 5. The curvilinear members may be attached to the free edges along the entire circumference (FIG. 6B).

In an alternative embodiment of the prosthesis (descending aorta module) 15, the prosthesis is provided with one or more apertures 16,17 in its wall as illustrated in FIG. 7A and FIG. 7B Each aperture is reinforced along its entire circumference with a flat doughnut-shaped patch 18 of a non-elastic, polymer with low resistance to plastic deformation (FIGS. 8A, 8B, 8C). The patch 18 may incorporate a radio-opaque or ferromagnetic substance to facilitate detection with radiography and magnetic resonance imaging respectively.

Figure 9B:
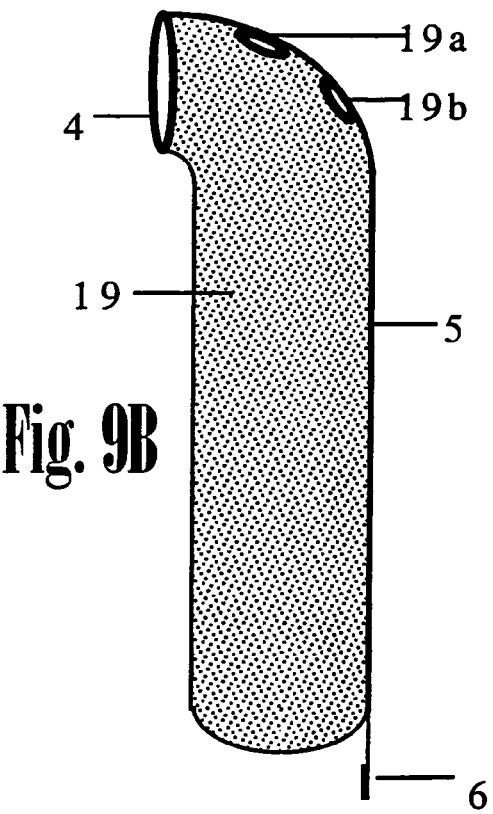
FIG. 9B is a perspective view of an alternative embodiment of the implantable prosthesis with multiple apertures, characterized by curvilinear members attached to the leading free edge of the prosthesis along the entire circumference
Figure 10A:
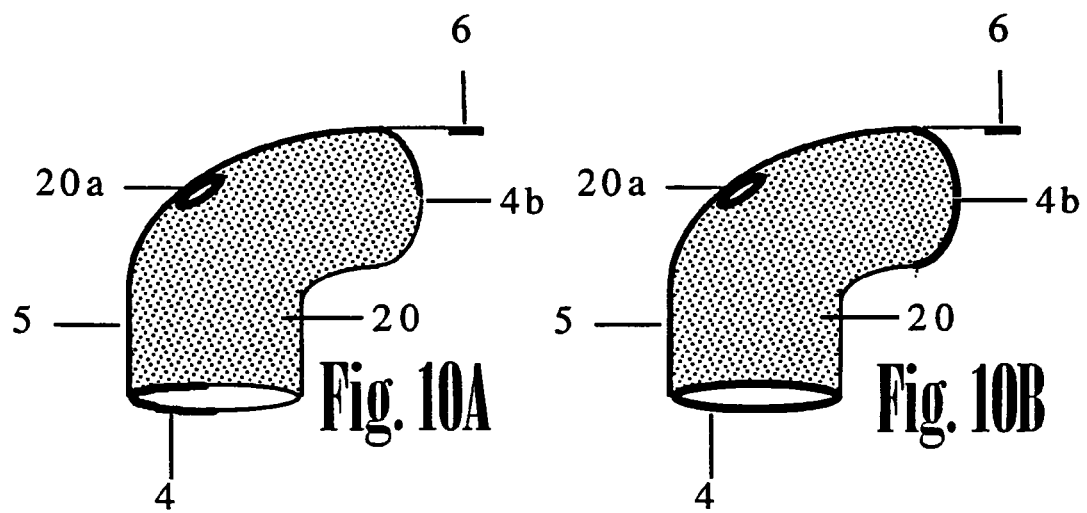
FIG. 10A is a perspective view of an alternative embodiment of the implantable prosthesis with a single aperture
Figure 10B:
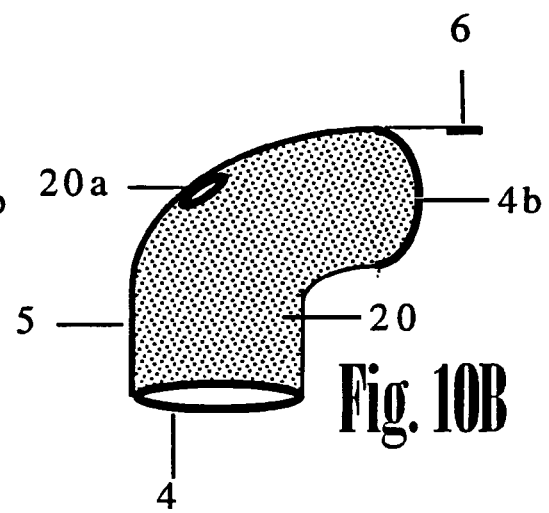
FIG. 10B is a perspective view of an alternative embodiment of the implantable prosthesis with a single aperture, characterized by curvilinear members attached to both free edges of the prosthesis along the entire circumference

Alternative embodiments of the prosthesis with aperture have the configurations illustrated in FIGS. 9A and 9B (aortic arch-descending aorta module) 19 and FIGS. 10A and 10B (ascending aorta-aortic arch module) 20 respectively. The aortic arch-descending aorta module 19 has two apertures, 19a,19b. The ascending aorta-aortic arch module 20 has one aperture 20a. The ascending aorta-aortic arch module 20 is characterized by both free edges having one or more symmetricallly attached outwardly biased, flexible curvilinear members with good shape memory 4,4b symmetrically attached to the trailing edge of the prosthesis 20. At least one of the curvilinear members attached to each free edge is attached to or continuous with the supporting strut 5 (FIGS. 10A, 10B). The curvilinear members may be attached to the free edges along the entire circumference (FIGS. 9B,10B).

In an alternative embodiment of the prosthesis (iliofemoral module) 21 FIG. 11, the supporting strut 5 does not extend beyond the trailing edge of the prosthesis.

In an alternative embodiment of the prosthesis (branch artery module) 22 the trailing free end 23 of the prosthesis 22 has a larger diameter than the rest of the prosthesis thereby giving a flanged configuration (FIG. 12). To the trailing edge of the prosthesis 22 is symmetrically attached one or more outwardly biased, flexible curvilinear members with good shape memory 4b, at least one of which is attached to or continuous with the supporting strut 5. The curvilinear members 4b may be attached to the trailing free edge along the entire circumference.

The delivery tool 24 to implant the invention is represented by FIG. 13. It consists of a thin-wall catheter (locking catheter) 25, and an axially movable, luminal coaxial wire (detachment wire) 26 (FIGS. 14A,14B). The hub of the locking catheter 25 incorporates a Tuohy-Borst valve 27. The leading end 28 of detachment wire 26 may be recessed as illustrated in FIG. 15A. The length of the recess (locking recess) 29 exceeds by a small margin the length of the locking peg 6 (FIG. 15B). To the trailing end 30 of the detachment wire is attached a plug (detachment wire handle) 31. The trailing end of the supporting strut 5 is a tight fit within the lumen of the locking catheter 25 (FIGS. 14A, 14B), so that frictional forces secure the supporting strut 5 to the locking catheter 25. In an alternative embodiment, the locking catheter 25 snugly accommodates the detachment wire 26 and supporting strut 5, once the locking peg engages the locking recess 29 on the detachment wire 26, such that radial movement of the supporting strut with respect to the detachment wire 26 is substantially restricted, while axial movement of the locking catheter 25 over the detachment wire 26 is unhindered (FIG. 15B).

A commercially available introducer sheath fitted with a haemostatic valve and a female Luer hub is used to implant all embodiments of the prosthesis that do not have an aperture 1,7,10,13,21. Prostheses with apertures 15,19,20, are implanted with the dployment tool 32 represented by FIG. 16. It consists of a introducer catheter 33 (FIG. 17), and an inner, axially movable, coaxial stiffening catheter 34 with a central lumen 35 (FIG. 18). The leading end 36 of the introducer catheter 33 is concentrically flared. To the trailing end of the catheter is fitted a Tuohy-Borst valve 37 carrying a female Luer hub 38. The lumen of the introducer catheter 33 communicates with the lumen of the female Luer hub 38 via the Tuohy-Borst valve 37. Along the shaft 39 of the introducer catheter 33 are single or multiple side-ports 40,41 that spatially correspond to the apertures on the respective prosthesis, when the prosthesis is radially compacted. The side-ports 40,41 extend linearly to the leading end 36 of the introducer catheter 33 in the form of narrow slits 42,43 (FIGS. 17,19,20,21). The stiffening catheter 34 has one or multiple side-ports (FIG. 18), that spatially correspond to the sideports 34a, 34b of the introducer catheter 33 (FIGS. 19,20,21). The leading segment 44 of the stiffening catheter 34 tapers to a cone-shaped expansion 45 at the tip. At the base of the cone-shaped expansion 45, is a circumferential sulcus 46 surrounding the leading segment 44 of the stiffening catheter 34 at its junction with the cone-shaped expansion 45 (FIG. 22). Prior to use, the stiffening catheter 34 is coaxially placed in the introducer catheter. The leading end 36 of the introducer catheter 33 is engaged in the circumferential sulcus at the base of the cone-shaped expansion 45 on the tip of the stiffening catheter 34, and the Tuohy-Borst valve 37 tightened around the stiffening catheter 34 (FIGS. 19,21). With the leading end 36 of introducer catheter 33 engaged in the circumferential sulcus 46, the introducer catheter 32 presents a streamlined profile.

Use of the Invention

The procedure for using the invention will be explained with reference to implantation in the aorta for the purpose of simplicity alone. As will be clear to anyone skilled in the art, the use of the invention and the method for implantation is not limited to this organ alone.

I. Preparation for Implantation:

A. Loading on to Delivery Cartridge:

It is anticipated that this step will be performed at the site of manufacture before the device is sterilised.

Figure 23:
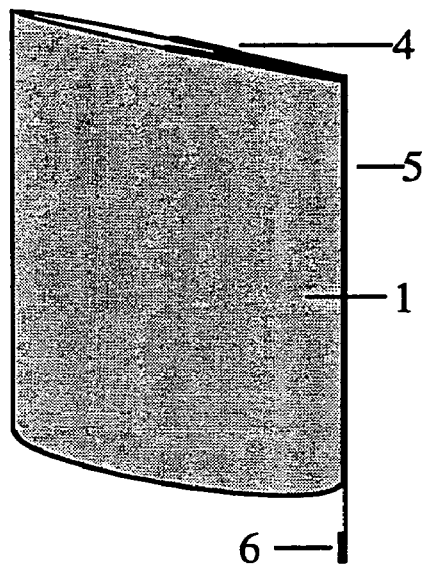
FIG. 23 is a perspective view of the implantable prosthesis being prepared for insertion in its loading cartridge

To facilitate introduction into the body, the prosthesis is flattened (FIG. 23) and tightly rolled such that it presents the lowest possible profile.

Figure 24:
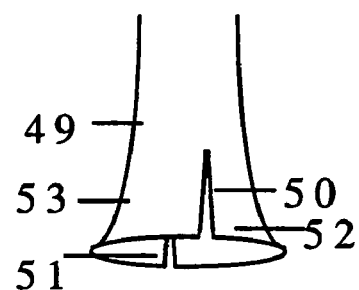
FIG. 24 is a perspective view of trailing end of a loading cartridge
Figure 25A:
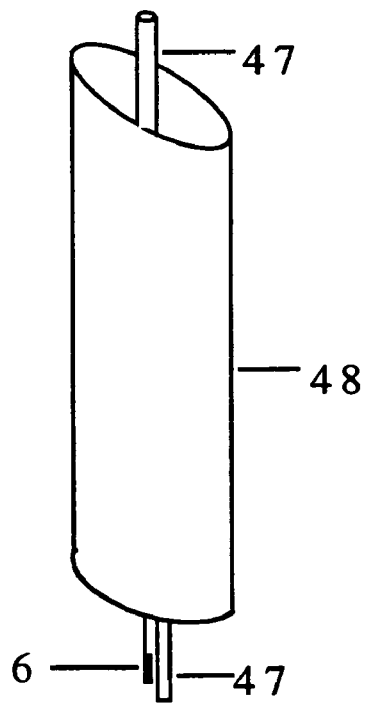
FIG. 25A is a perspective view of a loading cartridge containing an implantable prosthesis
Figure 25B:
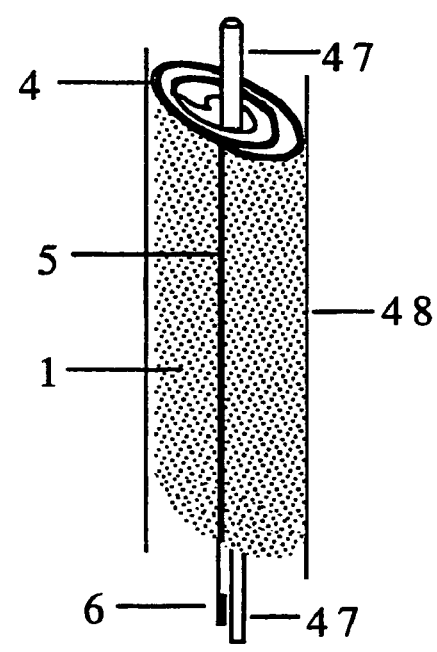
FIG. 25B is a perspective view partly in section of a loading cartridge containing an implantable prosthesis

In the case of embodiments of the prosthesis without branches or aperture 1,21,22 a short thin-wall cannula 47 is placed adjacent and parallel to the supporting strut 5, and the prosthesis rolled around them so that the cannula is coaxial to the prosthesis. A thin-wall polymer tube serves as the loading cartridge 48. The trailing end 49 of the cartridge 48 is flared and its free edge has two symmetrically placed slits 50,51 extending a short distance along the length of the loading cartridge 48, creating two flaps 52,53 (FIG. 24). By applying traction on the flaps 52,53 perpendicular to the longitudinal axis of the loading cartridge 48, the latter can be split into two separate parts. The loading cartridge 48 is drawn over the prosthesis to prevent it from unravelling (FIGS. 25A, 25B).

In the case of the aorto-bifemoral prosthesis 7, the coaxial cannula 47 is placed through the limb ipsilateral to the side of the detachment wire 26.

In the case of branched prostheses 10,13, a thin-wall cannula 47a,47b is introduced though each of the branches before the prosthesis is rolled up (FIG. 26).

In the case of prostheses with apertures 15,19,20, a flexible, thin-wall cannula 54 is placed through each aperture in the prosthesis (FIGS. 28,29). A third cannula may be placed coaxial to the lumen of the prosthesis. The prosthesis is rolled around the supporting strut 5. The loading cartridge 56 is a thin-wall tube with slits 57,58 spatially corresponding to the position of the cannulae (FIG. 27). The loading cartridge 56 is drawn over the rolled-up prosthesis such that cannula 54 engages the respective slit 57 (FIGS. 28,29).

B. Mating the Prosthesis to the Delivery Tool:

The trailing end of the supporting strut 5 is forcibly inserted into the lumen of the leading end of the locking catheter 25 (FIG. 14A). In an alternative embodiment of the prosthesis, the locking peg 6 of the prosthesis is engaged in the locking recess 29 of the detachment wire 26, and the locking catheter 25 advanced until tip of the detachment wire 26 is within its lumen (FIG. 15B). The Tuohy-Borst valve 27 of the locking catheter 25 is tightened, securing the detachment wire 26 to the locking catheter 25, and thereby the prosthesis to the delivery system 24 (FIG. 30).

II. Implantation of Prosthesis:

A separate procedure is described for implanting each of the different embodiments in the vascular system are described. These represent only examples to illustrate some of the envisaged uses of the invention and do not limit in any way the scope of its application as set forth in this patent application. Furthermore the deployment of a single prosthesis per site is described. Multiple prostheses may be coaxially deployed using the same or similar procedure if warranted by the anticipated circumferential stresses at the site of the lesion, by using two access sites alternately.

Figure 31:
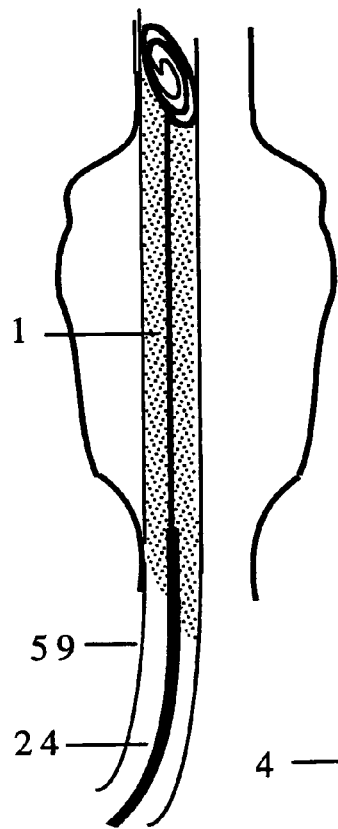
FIG. 31 is a perspective view partly in section of a implantable prosthesis being introduced into the abdominal aorta with an aneurysm
Figure 32:
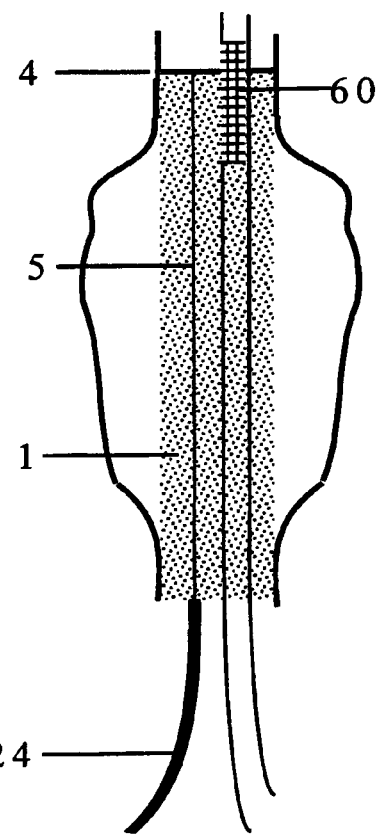
Figure 33:
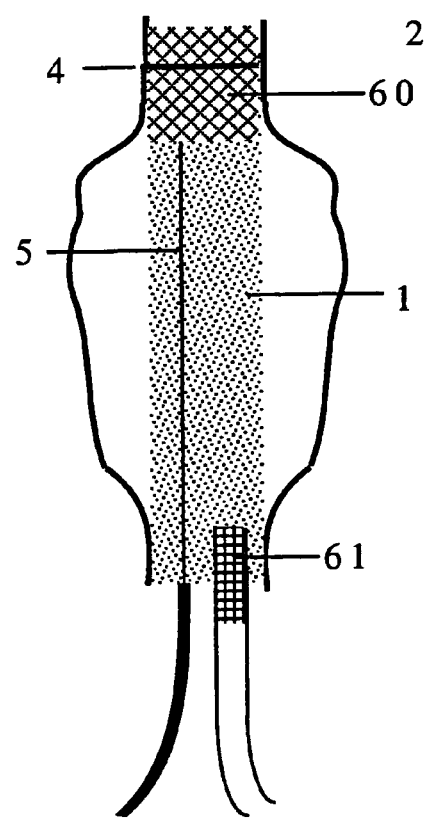

A. Implantation in the Infrarenal Aorta:

After the anatomy of the lesion has been satisfactorily determined, a guidewire is placed traversing the lesion. An introducer sheath 59 of appropriate calibre and length, with a hub of female Luer configuration attached to the haemostatic valve, is introduced coaxially over the guidewire and advanced until it spans the lesion. The guidewire and the introducer's dilator are removed. The loading cartridge 48 is introduced into the hub of the introducer sheath. Axial force is applied to the delivery tool 24 to backload the prosthesis 1 into the introducer sheath 59. Once the entire prosthesis 1 has passed beyond the haemostatic valve, the loading cartridge 48 is split as described above and removed. The prosthesis is advanced to the desired site under imaging guidance (FIG. 31). Holding the delivery tool 24 in place, the introducer sheath 59 is withdrawn exposing the leading edge 2 of the prosthesis 1. The curvilinear members 4 attached to the leading edge 2 regain their original shape, unrolling the prosthesis 1. The introducer sheath 59 is withdrawn further until the entire prosthesis is deployed (FIG. 32). Via another arterial access site, a guidewire is advanced coaxially through the prosthesis. A stent 60 is deployed across the leading edge of the prosthesis 1 using procedures well known to those skilled in the art, securing the prosthesis 1 to the vessel (FIG. 33). The Tuohy-Borst valve 27 of the delivery tool 24 is opened. The locking catheter 25 is withdrawn detaching the prosthesis from the detachment wire 26. The delivery tool 24 is withdrawn.

Another stent 61 is placed across the trailing edge of the prosthesis (FIG. 34). More stents 63 are place along the length of the prosthesis if deemed desirable (FIG. 35).

B. Implantation at the Aortic Bifurcation:

Deployment of the bifurcated prosthesis 7 is performed as explained above, ensuring that the entire device lies in the descending aorta. The prosthesis 7 is withdrawn, if desired, using the delivery tool 24, so that the prosthesis limb 7b contralateral to the detachment wire 26 enters its corresponding common iliac artery. Via the ipsilateral femoral artery, a guidewire is advanced coaxially through the prosthesis. A stent is deployed across the leading edge 2 of the prosthesis 7 securing it to the vessel. Another stent is placed overlapping the free edge of the ipsilateral limb 7b of the prosthesis. This step may be preceded by the placement of an iliofemoral module 21. In that case, another stent is placed overlapping the trailing edge of the latter. The bifurcated prosthesis 7 is detached from delivery tool 24. A stent is placed across the trailing edge of the prosthesis limb 7a on the same side. This step may be preceded by the placement of an iliofemoral module 21. In that case, another stent is placed overlapping the trailing edge of the latter. More stents are place to bridge the gaps between the previously placed stents if deemed desirable.

Aorto-biiliac lesions may be alternatively treated by placing two tubular prostheses 1 in parallel, with one prosthesis extending into each iliac artery (Sakaguchi S, et. al. Twin-tube endografts for aortic aneurysms: an experimental feasibility study. J Vasc Intervent Radiol 1999; 10:1092–98.)

Figure 38:
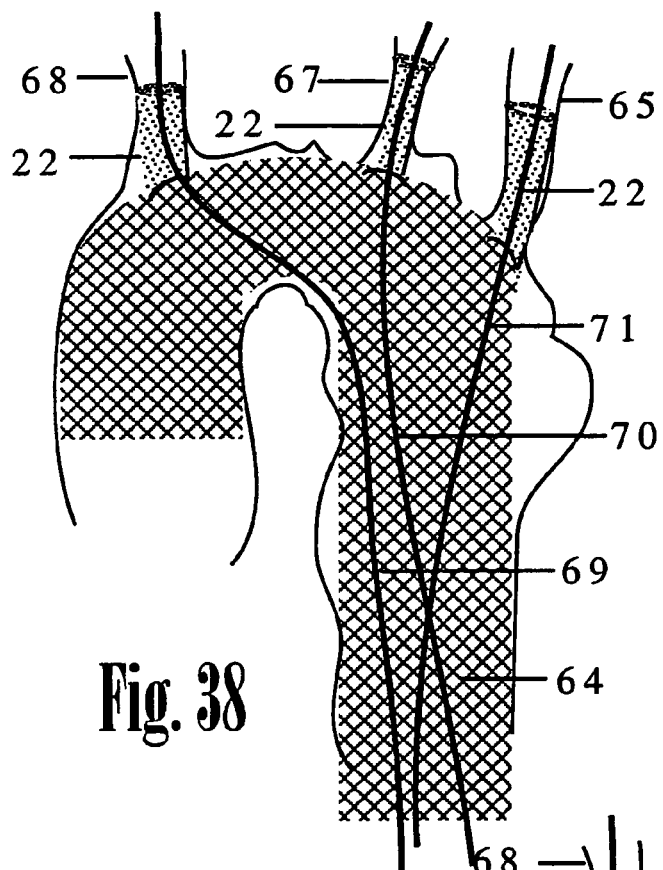

C. Implantation in the Aortic Arch and its Craniocerebral Branches:

(a) Implantation of Modular Prostheses:

One or multiple stents 64 are placed across the lesion (FIG. 36). A guidewire is advanced into the left subclavian artery 65. An angioplasty catheter 66 is advanced over the guidewire into the left subclavian artery 65. The position of the catheter 66 is adjusted so that the balloon straddles the wall of stent 64. The balloon is inflated to displace any stent strut crossing the ostium of the left subclavian artery 65 (FIG. 37). The balloon catheter 66 is withdrawn. Using techniques well known to those skilled in the art, a branch artery module 22 of appropriate size is implanted in the left subclavian artery 65, such that its flanged trailing edge 23 lies within the stent. A stent is placed in the prosthesis 22 to secure it in place. A branch artery module 22 is similarly placed in the left carotid 67 and in the brachiocephalic artery 68 via the same and contralateral access sites respectively. Stents are placed in the prostheses. The guidewires 69,70,71 are not removed (FIG. 38).

Another guidewire is placed in the descending aorta via the access used to place the branch artery module in the brachiocephalic artery 68. The stiffening catheter is placed in the introducer catheter and their hubs locked together. The trailing end of the guidewire is fed through the lumen of the stiffening catheter 34 until it exits from the hub of the stiffening catheter. Likewise, the trailing end of the guidewire 69 in the brachiocephalic artery 68 is fed through the sideports of the introducer catheter 33 and stiffening catheter 35. The introducer catheter is advanced over the guidewires until the sideport of the introducer catheter is at the level of the ostium of the brachiocephalic artery 68. The Tuohy-Borst valve 37 in the hub of the introducer catheter 33 is partially opened. The stiffening catheter 34 is advanced slightly to disengage the tip 36 of the introducer catheter 37. The stiffening catheter 35 is then withdrawn with its coaxial guidewire.

Figure 39:
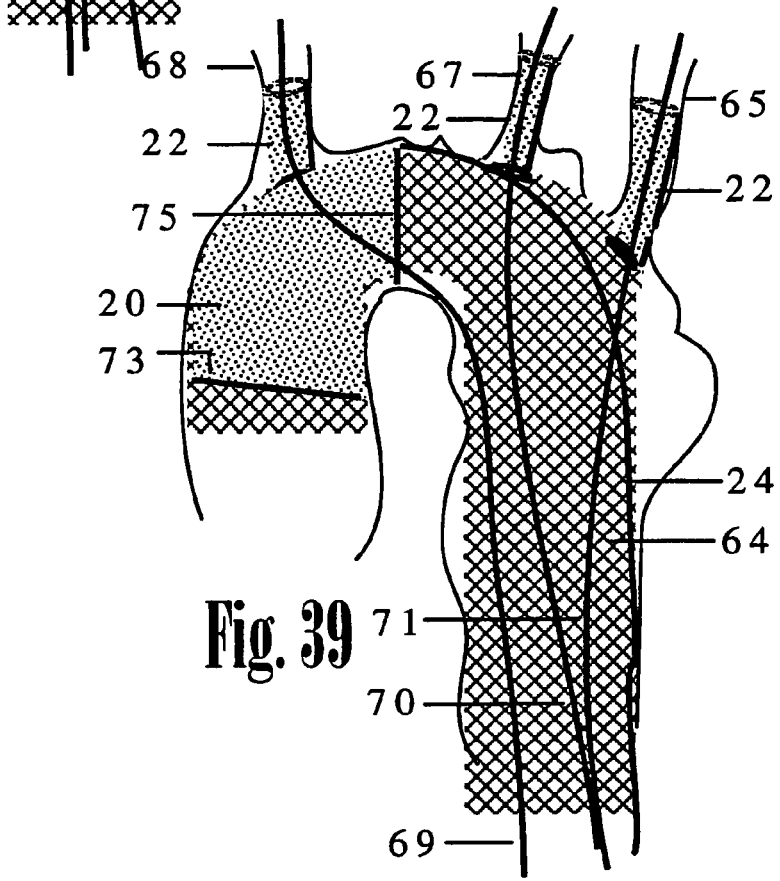
Figure 40:
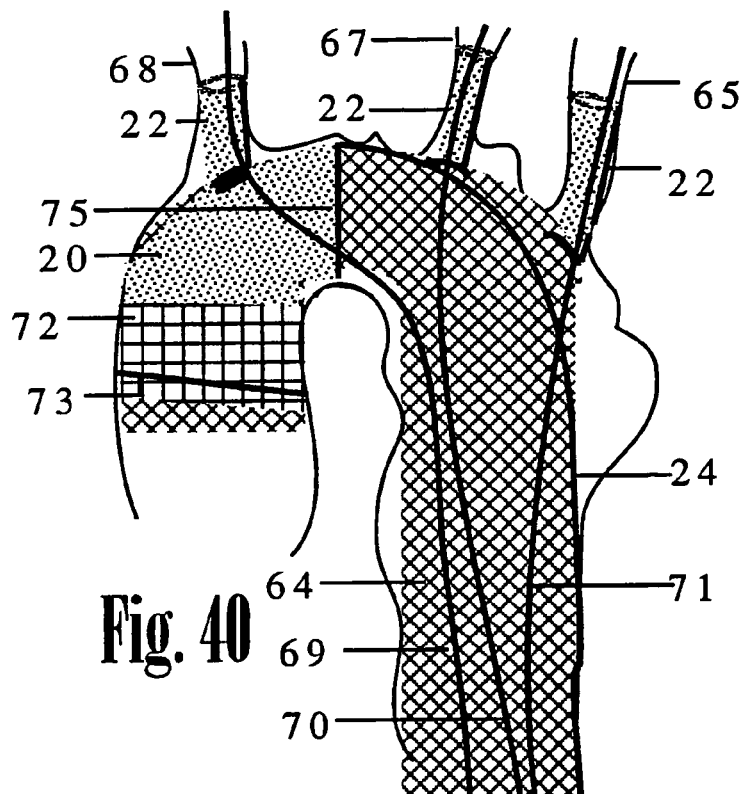
Figure 41:
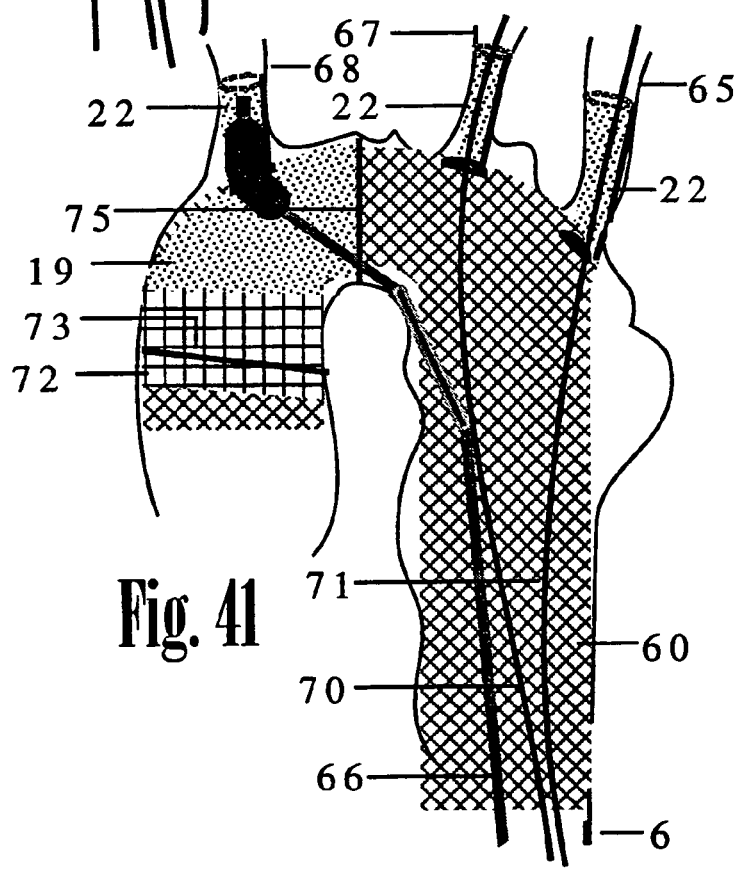
Figure 42:
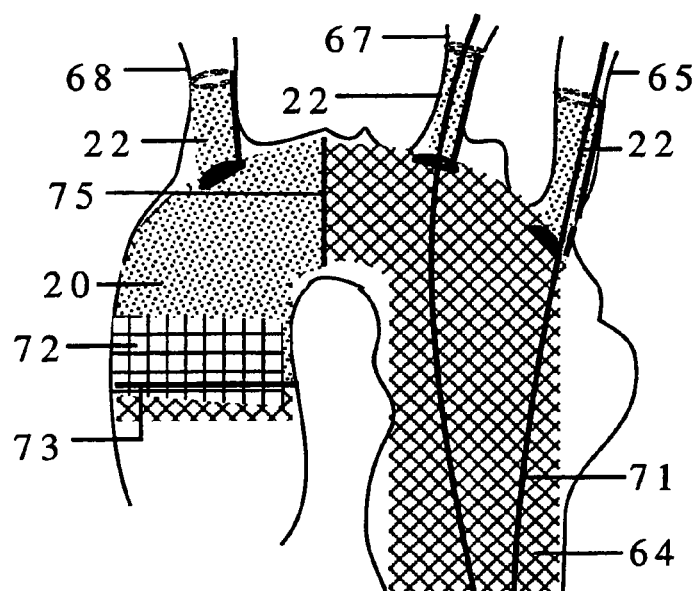

The trailing end of the guidewire 69 in the brachiocephalic artery 68 is fed through the cannula 54 lying in the slit 57 of a cartridge containing an ascending aorta-aortic arch module 20. The cannula is removed and the prosthesis 20 is introduced in the hub 38 of the introducer catheter 34. The Tuohy-Borst valve 37 is opened, and the prosthesis 20 backloaded into the introducer catheter 34, and the loading cartridge 56 removed. The prosthesis 20 is advanced until the aperture on the prosthesis is at the level of the ostium of the brachiocephalic artery 68. The introducer catheter 34 is withdrawn, deploying the prosthesis 20 (FIG. 39). Via the contralateral femoral artery, a stent 72 is placed overlapping the leading free edge 73 of the prosthesis 20, and securing it in place (FIG. 40). The prosthesis 20 is detached from the delivery tool 24, and the latter withdrawn. An angioplasty catheter 66 is advanced into ostium of the prosthesis 20 in the brachiocephalic artery 68 over the guidewire in situ. The balloon is inflated to dilate the aperture of the prosthesis 20 (FIG. 41). The angioplasty catheter is withdrawn (FIG. 42).

The trailing end of the guidewire lying with its tip in the aorta is fed through the lumen of the stiffening catheter 34 of an introducer catheter 32, with two side-ports until it exits from the hub of the stiffening catheter. Likewise, the trailing end of each of the guidewires 70,71 in the left carotid artery 67 and left subclavian artery 65 is fed through the appropriate sideport of the introducer catheter 33 and its coaxial stiffening catheter 34. The introducer catheter-stiffening catheter ensemble is advanced over the guidewires until the sideports of the introducer catheter and stiffening catheter are at the level of the corresponding branch vessel ostium. The Tuohy-Borst valve 37 in the hub of the introducer catheter 33 is partially opened. The stiffening catheter 34 is advanced slightly to disengage the tip 36 of the introducer catheter 33, and then withdrawn with its coaxial guidewire.

Figure 43:
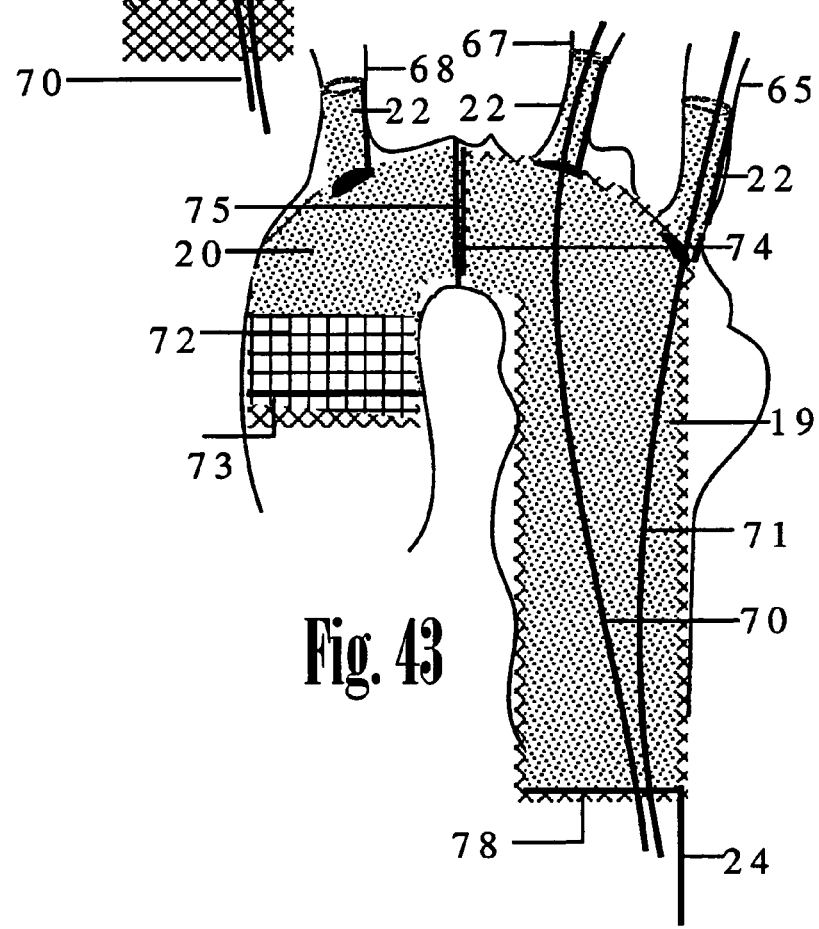
Figure 44:
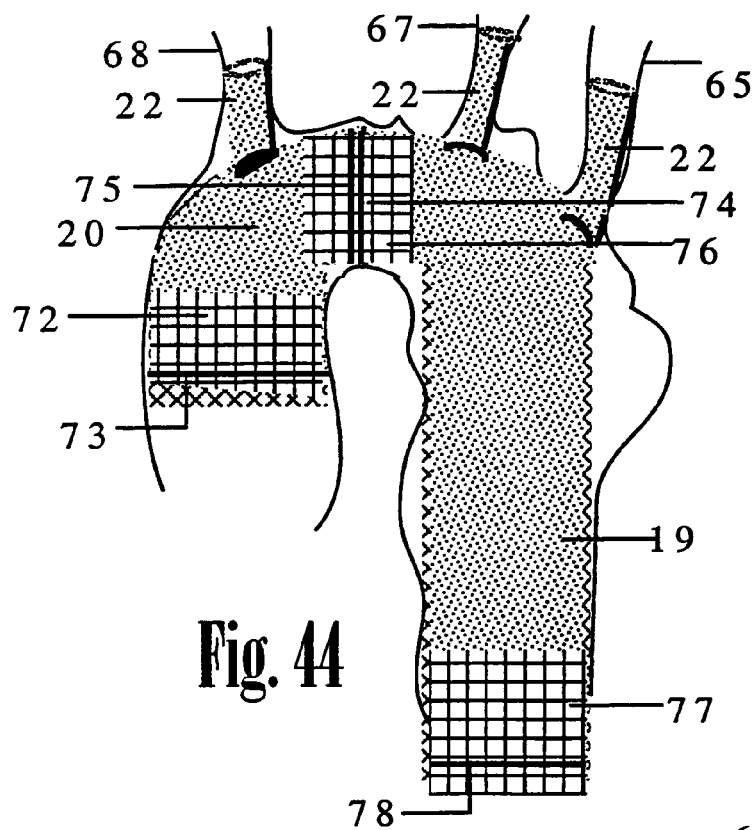
Figure 45:
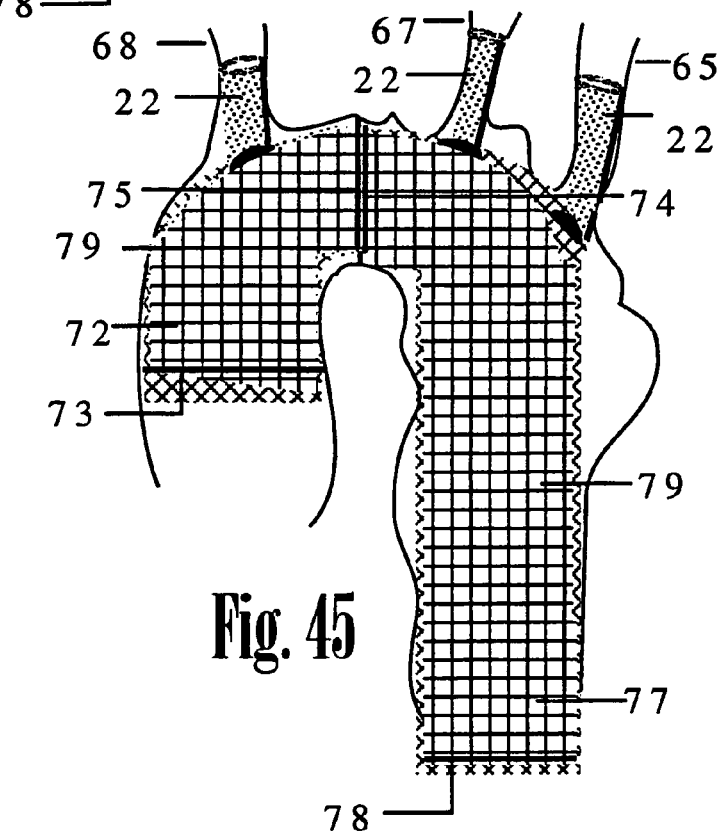

The trailing end of each of the guidewires 70,71 in the left carotid 67 and subclavian arteries 65 is fed through the appropriate cannula 54,55 in the slits 50/51 of a cartridge containing an aortic arch-descending aorta module 19. The cannulae are removed. The prosthesis 19 is backloaded into the introducer catheter 33 as described for a prosthesis without apertures. The prosthesis 19 is advanced until the each sideport 40,41 is at the level of the corresponding branch ostium. The introducer catheter 33 is partially withdrawn, deploying the prosthesis with its leading edge 74 overlapping the trailing edge 75 of the prosthesis 20 already in situ (FIG. 43). An angioplasty catheter is introduced into the aorta over the guidewire 70 and placed straddling the ostium of the left carotid artery 67. The balloon is inflated dilating the corresponding aperture of the implanted prosthesis 19. The same procedure is repeated for the left subclavian artery 65. Via the femoral artery contralateral to that used to place the prosthesis 19, a stent 76 is placed overlapping the leading free edge 74 of the aortic arch-descending aorta module 19 securing it in place (FIG. 44). The delivery tool is detached from the prosthesis 19 and withdrawn. Another stent 77 is placed overlapping the trailing edge 78 of the prosthesis 19 (FIG. 44). More stents 79 are placed if deemed necessary (FIG. 45). Repeat dilatation of the ostium of the craniocerebral branches may be performed using, procedures familiar to those skilled in the art, if deemed necessary.

Figure 46:
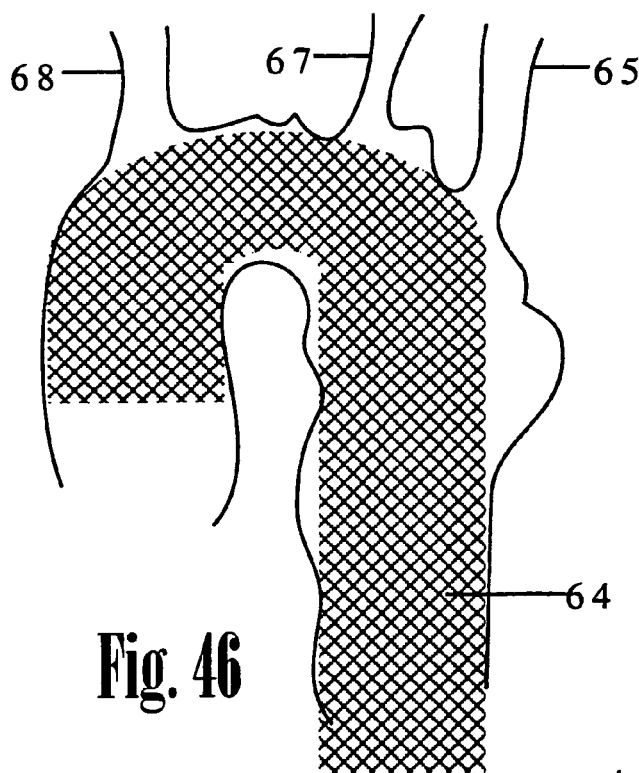
FIGS. 46 to 53 are longitudinal sectional views illustrating an alternative procedure for implanting prostheses in a thoracoabdominal aorta with an aneurysm involving the craniocerebral branches according to the invention
Figure 47:
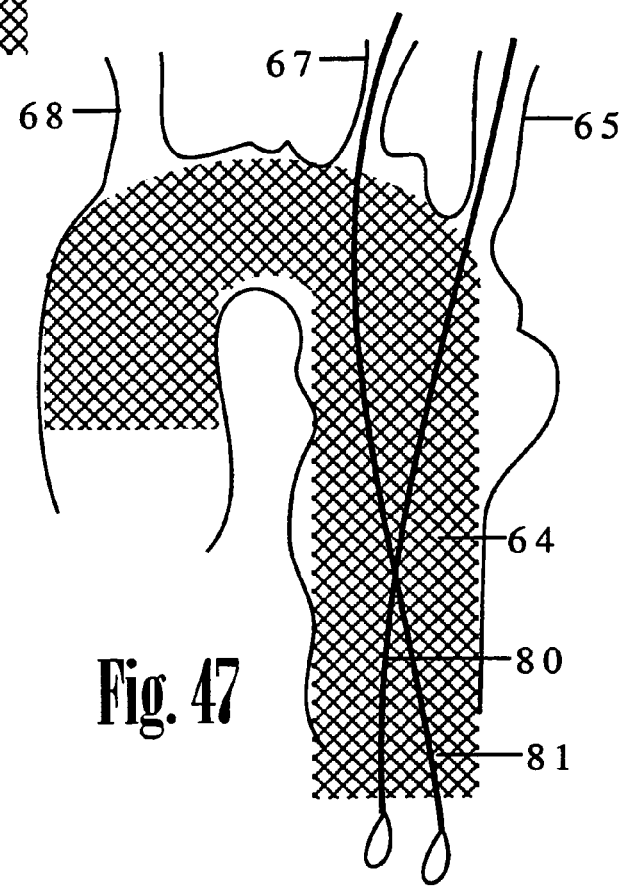
Figure 48:
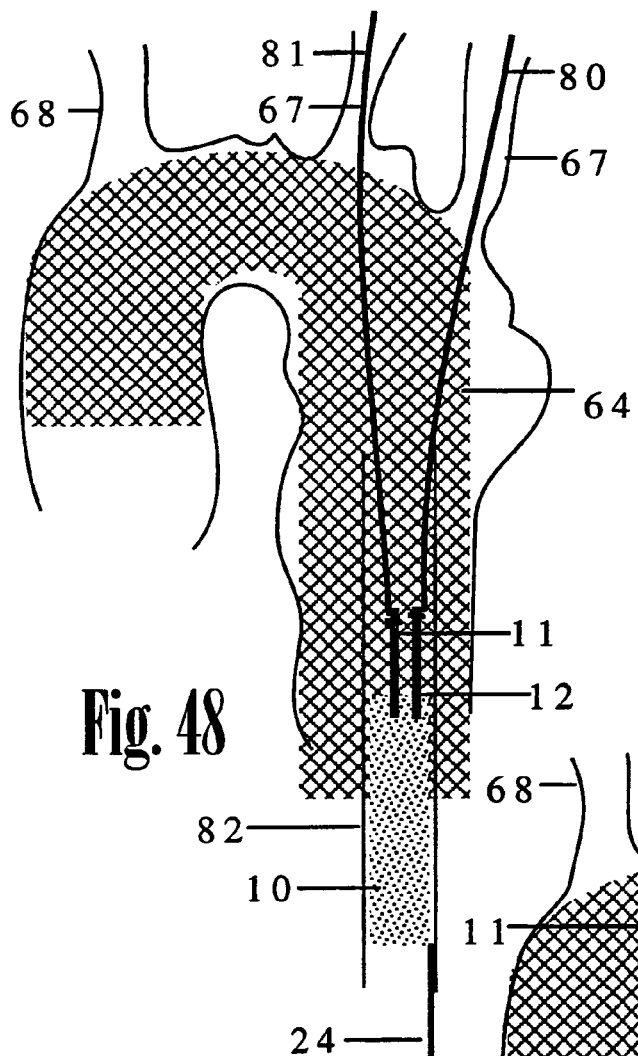
Figure 49:
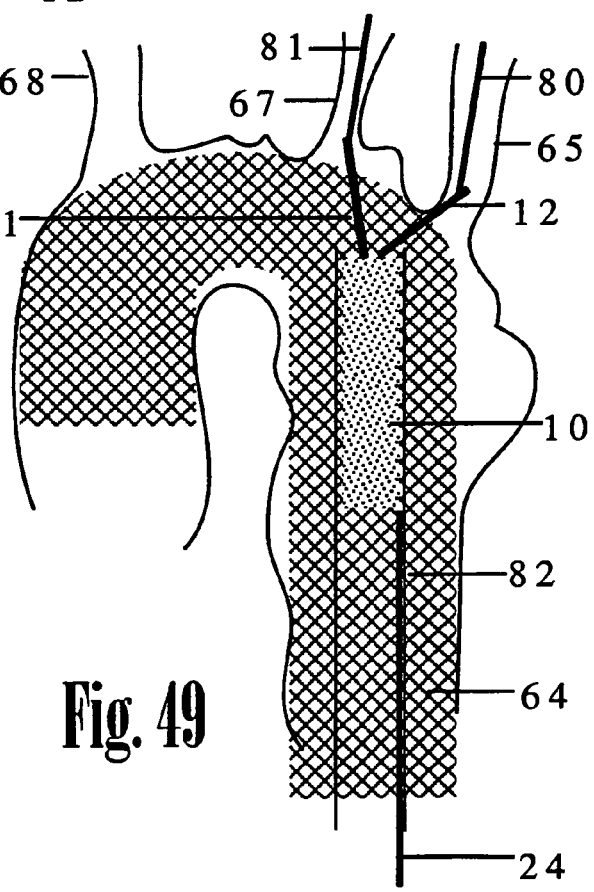
Figure 50:
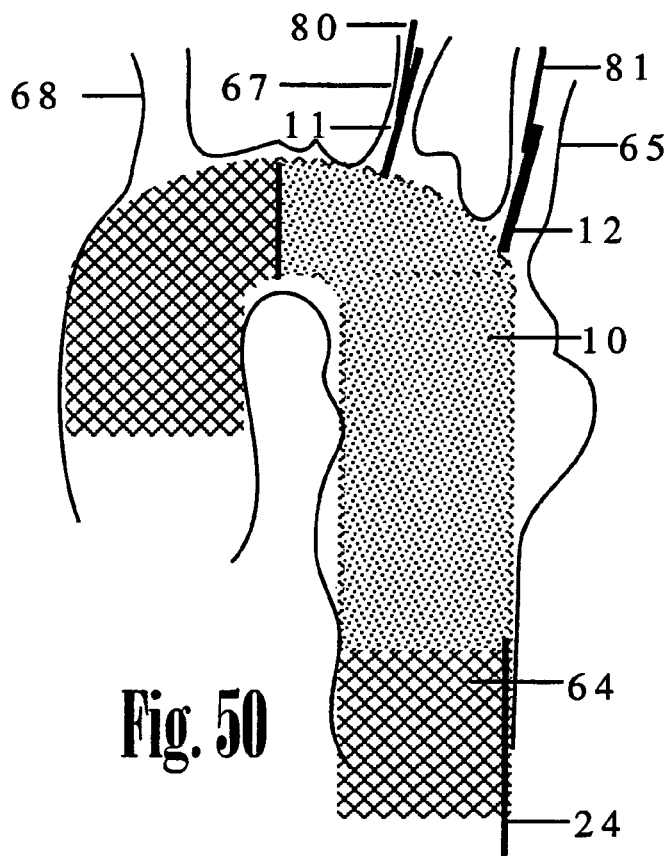
Figure 51:
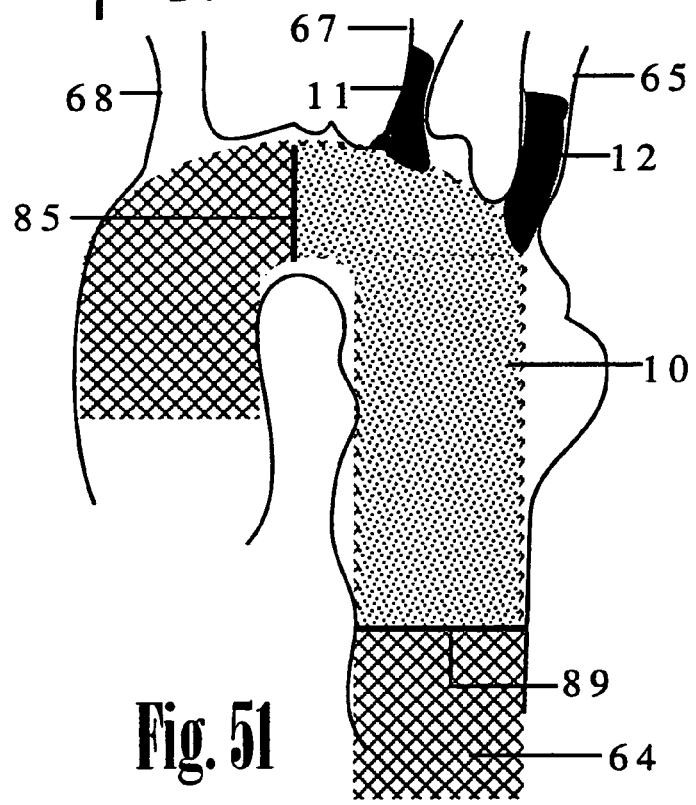
Figure 52:
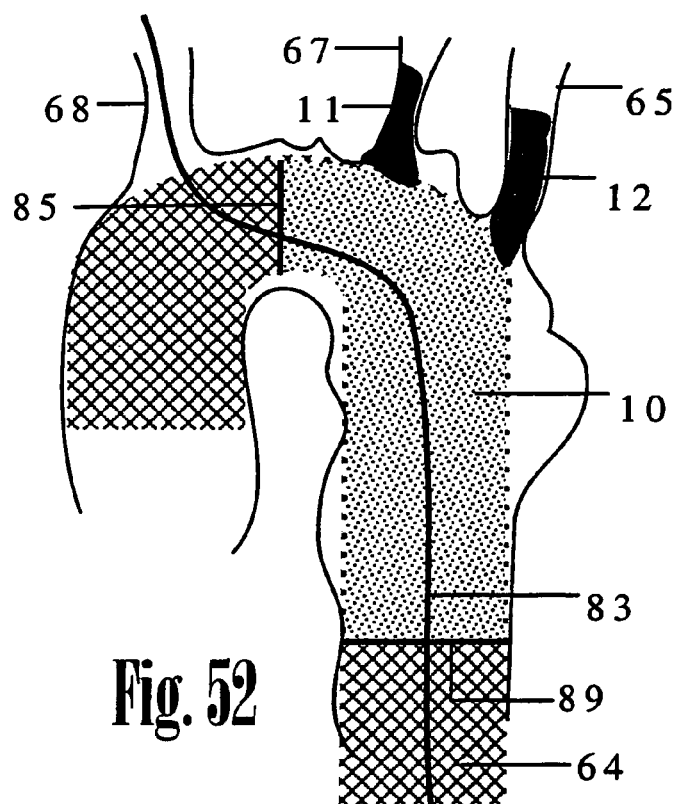
Figure 53:
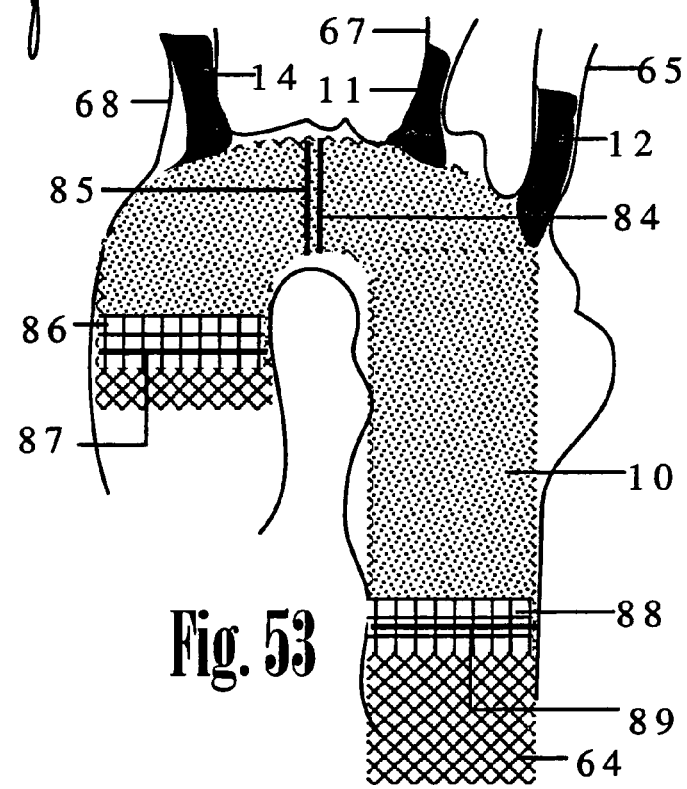

(b) Implantation of Branched Prostheses:

One or multiple stents 64 are placed spanning the lesion (FIG. 46). Via the left carotid artery 67, and via the left subclavian artery 65, two microsnares 80,81 are placed in the aorta using procedures familiar to those skilled in the art (FIG. 47). Via an introducer sheath placed in one common femoral artery, a loop snare is placed in the aorta. Using this loop snare, the two microsnares 80,81 are exteriorised. The introducer sheath 82 is advanced until its tip was immediately peripheral to the ostium of the left subclavian artery 65. Each microsnare is placed around the corresponding limb 11,12 of an aortic arch-descending aorta branched prosthesis 10, loaded in its cartridge 48. The snares are tightened and branched prosthesis 10 is backloaded into the introducer sheath 83 (FIG. 48). In synchrony, the microsnares 80,81 are withdrawn and the aortic arch-descending aorta branched prosthesis 10 advanced until each prosthesis limb 11,12 has entered its respective branch artery (FIG. 49). The introducer sheath 82 is withdrawn. The microsnares 80,81 are withdrawn further and the delivery tool 24 advanced in tact until a satisfactory orientation of the aortic arch-descending aorta branched prosthesis 10 is achieved (FIG. 50). The prosthesis limbs 10,11, are released allowing them to open (FIG. 51). Via the femoral artery contralateral to that used to place the branched prosthesis 10, a stent is placed in each prosthesis limb 11,12, securing it in place. The aortic arch-descending aorta branched prosthesis 10 is detached from the delivery tool 24, and the latter withdrawn. Via the brachiocephalic artery 68, a microsnare 83 is introduced into the aorta (FIG. 52). Using the procedure described for aortic arch-descending aorta branched prostheses 10, an ascending aorta-aortic arch branched prosthesis 13 is implanted ensuring That its trailing edge 84 overlaps the leading edge 85 of the previously implanted aortic arch-descending aorta branched prosthesis 10. A stent 86 is placed overlapping the leading edge 87 of the ascending aorta-aortic arch branched prosthesis 13. The prosthesis 13 is detached from the delivery tool 24, and the latter withdrawn. Another stent 88 is placed across the trailing edge 89 of the aortic arch-descending aorta prosthesis 10 (FIG. 53). More stents are placed along the length of the prosthesis if deemed necessary.

What is claimed is:

1. A device for transluminal treatment of lesions of tubular organs, comprising:
   (a) an implantable uni- or multilamellar tubular prosthesis with a leading end limited by a leading free edge, and a trailing end limited by a trailing free edge, and a body in between the leading free edge and the trailing free edge, and to which is attached a linear member with a leading end and a trailing end, wherein said trailing end of said linear member is provided with a short peg that has a more prominent profile in cross-section than the linear member,
   whereby said prosthesis is provided with longitudinal support, and, said linear member is continuous with or bonded to one or more outwardly biased, flexible curvilinear members having good shape memory, and,
   each curvilinear member has at least one free end, and said free end does not overlap the free end of another curvilinear member when the prosthesis is not radially compressed, and,
   said one or more curvilinear members are symmetrically attached to the leading free edge of said prosthesis, the radius of curvature of said curvilinear members being equal to the radius of curvature of the prosthesis, whereby said prosthesis is provided with radial support, and,
   said prosthesis being additionally characterised by a resilient connection between said linear supporting member and at least one curvilinear member, whereby the angle between the said linear supporting member and the said curvilinear member can be reversibly altered by the application of force perpendicular to the plane described by said curvilinear members, and,
   (b) a deployment instrument for endoluminally implanting said prosthesis comprising:
      (i) a deployment tool comprising an outer introducer catheter with a leading end limited by a leading edge, and a removable liner, coaxial, rigid catheter with a leading end limited by a leading edge, and,
      (ii) a delivery tool, which can be detachably fixed to said prosthesis by ex vivo manipulation, whereby said prosthesis can be temporarily held stationary within a tubular organ during implantation, and wherein said delivery tool is comprised of:
         1. a narrow thin-walled catheter with a leading end and a trailing end, characterised by a Tuohy-Borst valve attached to said trailing end, and,
         2. an axially movable linear detachment member with a leading end and a trailing end, housed within said thin-walled catheter, and characterised by:
            ($\alpha$) being longer than said thin-walled catheter, and,
            ($\beta$) being provided with a recess that can accommodate the peg attached to the trailing end of the linear supporting member of the prosthesis.

2. A device according to claim 1, wherein two or more magnetised linear members are symmetrically attached to the prosthesis parallel to its longitudinal axis with their magnetic force fields are aligned in the same direction, whereby the prosthesis is provided with radial and longitudinal support, and said prosthesis exerts radial centrifugal force on radial compression.

3. A device according to claim 1, wherein the prosthesis is provided with two or more symmetrically arrayed linear deposits of magnetised powder parallel to the longitudinal axis of the prosthesis, the magnetic force fields of the magnetic deposits being aligned in the same direction, whereby the prosthesis is provided with radial and longitudinal support, and said prosthesis exerts radial centrifugal force on radial compression.

4. A device according to claim 3, wherein the magnetised powder is impregnated in a resorbable biocompatible matrix that is bonded to said prosthesis, whereby said prosthesis gradually loses its magnetism over time, whereby said prosthesis becomes suitable for in vivo examination using magnetic resonance techniques.

5. A device according to claim 1, wherein the trailing end of the linear supporting member extends beyond the trailing end of the prosthesis.

6. A device according to claim 1, wherein the trailing end of the linear supporting member is provided with a short cylindrical peg that has a more prominent profile in cross-section than the prosthesis than the supporting member.

7. A device according to claim 1, wherein the linear supporting member protrudes beyond the leading free edge of the prosthesis and is continuous or bonded to an additional one or more outwardly biased, flexible curvilinear members whose radius of curvature is equal to or larger than the luminal radius of the prosthesis, and which are not continuous with the leading edge of the prosthesis.

8. A device according to claim 1, wherein the curvilinear members are made of a thermodynamic material with a transitional temperature range below the normal human body temperature.

9. A device according to claim 1, wherein the trailing end of the prosthesis is bifurcated into a first limb and a second limb to form a crotch, and a linear member bent into "V" shape with an apex is bonded to the two limbs of the prosthesis, whereby the apex of the "V" supports the crotch of the prosthesis.

10. A device according to claim 1, wherein the leading end of said prosthesis is curved, and one more tubular extensions with a free edge are provided that are luminally continuous with the prosthesis, whereby the configuration of the said prosthesis resembles the anatomy of the structure in which said prosthesis is being implanted, and that each tubular extension is supported by a linear member that is continuous with or bonded to one or more outwardly biased, flexible curvilinear members with good shape memory, that are symmetrically attached to the free edge of said tubular extension, the radius of curvature of said curvilinear members being equal to the radius of curvature of said tubular extension.

11. A device according to claim 10, wherein to the trailing edge of said prosthesis is symmetrically attached one or more outwardly biased, flexible curvilinear members with good shape memory at least one of which is continuous with or bonded to the linear supporting member, whereby the angle between the said linear supporting member and the said curvilinear member can be reversibly altered by the application of force perpendicular to the plane described by the said curvilinear members.

12. A device according to claim 1, wherein said prosthesis is provided with one or more apertures in the body, said aperture being characterised by reinforcement along its entire circumference with a non-elastic, material with low resistance to plastic deformation, whereby the size of the aperture can be increased as desired in vivo with the use of an expansile device such as a balloon angioplasty catheter.

13. A device according to claim 1, wherein to the trailing edge of the prosthesis is symmetrically attached, one or more, outwardly biased, flexible, curvilinear members, and each of said curvilinear members is characterised by good shape memory and at least one free end, and said free end does not overlap the free end of another curvilinear member when the prosthesis is not radially compressed, and at least one of said curvilinear members is continuous with or bonded to the linear supporting member in resilient fashion, whereby the angle between said linear supporting member and the said curvilinear member can be reversibly altered by the application of force perpendicular to the plane described by the said curvilinear members.

14. A device according to claim 1, wherein the trailing end of the prosthesis is of a wider diameter than the rest of the prosthesis, and wherein to the trailing edge of the prosthesis is symmetrically attached one or more, outwardly biased, flexible curvilinear members with good shape memory, at least one of which is continuous with or bonded to the linear supporting member in resilient fashion, whereby the angle between the said linear supporting member and the said curvilinear member can be reversibly altered by the application of force perpendicular to the plane described by the said curvilinear members.

15. A device according to claim 1, wherein longest cross-sectional diameter of lumen of the thin-walled catheter closely approximates the longest cross-sectional diameter of the trailing end of the linear supporting member of the prosthesis, whereby said trailing end can be displaced out of said thin-walled catheter only by the application of axial force along the long axis of the said trailing end.

16. A device according to claim 1, wherein the lumen of the thin-walled catheter snugly accommodates the leading end of the linear detachment member and the trailing end of the linear supporting member of the prosthesis, when the peg of the said supporting member is engaged in the recess of the said detachment member, whereby the prosthesis is attached to the delivery tool.

17. A device according to claim 1, wherein:
(a) the leading end of the outer introducer catheter is flared and the catheter is provided with one or more sideports, each of said side-ports extending in the form of a narrow slit to the leading edge of the outer introducer catheter, and,
(b) the coaxial rigid catheter has a central lumen and one or more side-ports, and the said side-ports spatially correspond to the side-ports of the outer introducer catheter, and,
(c) the leading end of the rigid coaxial catheter tapers towards the leading end of the said rigid coaxial catheter, and the tapering segment abruptly gives way to a concentric conical enlargement with a base, the said base of said conical enlargement being provided with a circular sulcus to accommodate the free leading edge of the introducer catheter, whereby the introducer catheter presents a smooth profile when the said free edge is engaged in the said sulcus of the coaxial rigid catheter.

* * * * *